(12) United States Patent
Kumar et al.

(10) Patent No.: US 8,388,570 B2
(45) Date of Patent: *Mar. 5, 2013

(54) CONTROLLED TISSUE CAVITY DISTENDING SYSTEM WITH MINIMAL TURBULENCE

(76) Inventors: Atul Kumar, Jaipur (IN); Alka Kumar, Jaipur (IN)

( * ) Notice: Subject to any disclaimer, the term of this patent is extended or adjusted under 35 U.S.C. 154(b) by 852 days.

This patent is subject to a terminal disclaimer.

(21) Appl. No.: 11/211,489

(22) Filed: Aug. 26, 2005

(65) Prior Publication Data

US 2006/0047240 A1    Mar. 2, 2006

(30) Foreign Application Priority Data

Aug. 27, 2004   (IN) ............................ 1621/DEL/2004

(51) Int. Cl.
*A61M 1/00*     (2006.01)
*A61M 31/00*    (2006.01)
(52) U.S. Cl. ................ 604/30; 604/19; 604/48; 604/65; 604/151; 604/246; 604/250
(58) Field of Classification Search ................... 604/19, 604/27–34, 46, 48, 49, 65–67, 93.01, 118, 604/119, 131, 244, 246, 250, 257, 41, 43, 604/151, 154
See application file for complete search history.

(56) References Cited

U.S. PATENT DOCUMENTS

| | | | |
|---|---|---|---|
| 3,599,639 A * | 8/1971 | Spotz ........................... | 604/119 |
| 4,261,360 A | 4/1981 | Perez | |
| 4,624,625 A * | 11/1986 | Schrenker ........................ | 417/20 |
| 4,650,462 A * | 3/1987 | DeSatnick et al. .............. | 604/30 |
| 4,685,331 A * | 8/1987 | Renken et al. ............. | 73/204.15 |
| 4,902,277 A * | 2/1990 | Mathies et al. .................. | 604/67 |
| 4,921,477 A * | 5/1990 | Davis .............................. | 604/22 |
| 5,041,096 A | 8/1991 | Beuchat et al. | |
| 5,066,282 A * | 11/1991 | Wijay et al. .................... | 604/152 |
| 5,464,391 A | 11/1995 | Devale | |
| 5,556,378 A | 9/1996 | Storz et al. | |
| 5,605,545 A | 2/1997 | Nowosielski et al. | |
| 5,616,121 A * | 4/1997 | McKay .......................... | 604/30 |
| 6,283,937 B1 * | 9/2001 | Takamatsu et al. ............. | 604/31 |
| 6,997,896 B2 * | 2/2006 | Novak ............................ | 604/67 |

(Continued)

FOREIGN PATENT DOCUMENTS

EP            1 010 437        6/2000

*Primary Examiner* — Quynh-Nhu H Vu
(74) *Attorney, Agent, or Firm* — Dickstein Shapiro LLP

(57) ABSTRACT

The present invention provides a system and a method for distending a body tissue cavity of a subject by continuous flow irrigation by using a dynamic pump, such as a centrifugal pump, on the inflow side and a positive displacement pump, such as a peristaltic pump, on the outflow side, such that the amplitude of the pressure pulsations created by a the said outflow positive displacement pump inside the said tissue cavity is substantially dampened to almost negligible levels. The present invention also provides a method for accurately determining the rate of fluid loss, into the subject's body system, during any endoscopic procedure without utilizing any deficit weight or fluid volume calculation, the same being accomplished by using two fluid flow rate sensors. The present invention also provides a system of creating and maintaining any desired pressure in a body tissue cavity for any desired cavity outflow rate. The system and the methods of the present invention described above can be used in any endoscopic procedure requiring continuous flow irrigation few examples of such endoscopic procedures being hysteroscopic surgery, arthroscopic surgery, trans uretheral surgery, endoscopic surgery of the brain and endoscopic surgery of the spine.

1 Claim, 7 Drawing Sheets

U.S. PATENT DOCUMENTS

2004/0030279 A1* 2/2004 Rubenstein et al. .............. 604/9
2006/0052666 A1* 3/2006 Kumar et al. ................. 600/159
2006/0122556 A1* 6/2006 Kumar et al. ................... 604/67
2006/0122557 A1* 6/2006 Kumar et al. ................... 604/67
2006/0129099 A1* 6/2006 Kumar et al. ................. 604/151
2007/0021713 A1* 1/2007 Kumar et al. ................... 604/27

* cited by examiner

CONTROLLED TISSUE CAVITY DISTENDING SYSTEM WITH MINIMAL TURBULENCE

FIELD OF INVENTION

The present invention relates to a system for distending body tissue cavities of subjects utilizing continuous flow irrigation during endoscopic procedures. The system and the methods of the present invention described above can be used in any endoscopic procedure requiring continuous flow irrigation few examples of such endoscopic procedures being hysteroscopic surgery, arthroscopic surgery, trans uretheral surgery (TURP), endoscopic surgery of the brain and endoscopic surgery of the spine. The proposed invention can also have certain useful non medical applications.

BACKGROUND OF THE INVENTION

Endoscopic surgery is becoming increasingly popular because of the following reasons:
(a) it is a minimally invasive form of surgery,
(b) it avoids large incisions over the skin and muscle,
(c) it is associated with less pain,
(d) there is a relatively less requirement of blood transfusions and
(e) the patients can return back to normal work relatively early with minimal loss of working days.

While in the corresponding open conventional surgeries a relatively large body part consisting of skin and muscle needs to be cut in order to gain access to an underlying body tissue cavity, in endoscopic surgery instead of cutting body structures like skin and muscle an endoscope is introduced into the body cavity via the natural opening of a cavity, if such exists, or alternatively a minute hole is made in the wall of the cavity through which the endoscope is introduced to visualize the interior of the body tissue cavity and to perform major or minor endoscopic surgical procedures. For this reason endoscopic surgery is also sometimes called 'key hole' or 'minimal access surgery'. Besides reducing the pain associated with surgery, endoscopic surgery also helps in reducing the medical expenses.

Endoscopic Surgery is Primarily Related to a Tissue Cavity:

All endoscopic surgeries are carried out on a existing body cavity which is distended or 'ballooned up' by a suitable distending apparatus which permits the inner lining of the said tissue cavity to be visualized by the help of an endoscope. Though multiple endoscopic procedures have become established as the preferred surgical modality but still there is immense scope of increasing the safety and efficiency of the such existing endoscopic procedures by improving upon the existing techniques and apparatus used for distending body tissue cavities. Hysteroscopy, arthroscopy, TURP (transuretheral resection of the prostate), endoscopic surgery of the brain and endoscopic surgery of the spine are few of the routinely performed endoscopic procedures and the organs related to such surgeries being uterus, human joints, bladder, brain and the spine respectively. The list of endoscopic surgeries is long, ever increasing and there is hardly any body organ or organ system to which the benefits of endoscopy have not been extended.

Tissue Cavitiy is Initially Collapsed in its Natural State:

In the natural state tissue cavities are collapsed structures and the cavity walls are in apposition with each other as if kissing each other. Thus if an endoscope is introduced in such a collapsed cavity no endoscopic visualization is possible unless the cavity is ballooned up by filling it with a transparent fluid or a gas. Such ballooning of a tissue cavity is technically termed as 'cavity distension'. No endoscopic procedure can be performed without an efficient cavity distending system and no endoscopic procedure should be attempted without a safe distending system because unsafe tissue cavity distending means can lead to extreme human morbidity and even the death of a patient and such grim realities shall be discussed in the later sections of this manuscript. Cavity distension provides both endoscopic visualization and mechanical distension which is necessary for the movement of endoscopic instruments.

Continuous Flow Irrigation:

In the present invention, the Inventors are focused on a system for distending body tissue cavities for those endoscopic procedures in which the cavity needs to be distended by utilizing continuous flow irrigation only. Here, the term 'continuous flow irrigation' means that fluid simultaneously enters and escapes from a tissue cavity via separate entry and exit points, as a result of which a positive fluid pressure is created inside the tissue cavity which distends the cavity.

The Need for Continuous Flow Irrigation:

Any tissue cavity can be easily distended in a 'static manner' by simply pushing fluid via a single inflow tube inserted into the cavity and in this manner a desired cavity pressure can be developed and also maintained. For example, a cavity can be distended by pressing on the piston of a simple syringe filled with fluid with the outlet end of the syringe being connected to the cavity by a tube. Alternatively a fluid filled bottle may be elevated to a suitable height and under the influence of gravity fluid from such bottle may be allowed to enter the cavity via a tube connecting the said bottle to the cavity and in this manner a desired static pressure can be developed and also maintained. Though it is very easy to achieve distension by the said static manner, it is not a practical solution because blood and tissue debris which are invariably released from the fragile cavity inner lining mix with the distending fluid and endoscopic vision gets clouded within a few seconds or a few minutes. Thus continuous flow irrigation is needed to constantly wash away blood and tissue debris in order to maintain constant clear endoscopic vision.

Cavity Pressure and Cavity Flow Rate:

It is obvious that cavity fluid pressure and the flow rate through the cavity are the two basic parameters associated with all continuous flow irrigation systems.

An Efficient Distending System:

The Inventors believe that an efficient distending system is the one which provides a predictably continuous clear visualization and a predictably stable mechanical stabilization of the cavity walls. In order to achieve this the Inventors believe that a suitable stable constant precise cavity pressure and a suitable stable precise cavity flow rate have to be created and maintained in a predictable and controlled manner. The cavity pressure should be adequate so that vision is not clouded by oozing of blood and enough mechanical separation of the cavity walls occurs to allow the movement of the endoscope. Similarly, the cavity flow rate should be adequate enough to constantly wash away blood and tissue debris in order to allow clear vision. Many prior systems utilize a peristaltic pump over the inflow and or the outflow side and these peristaltic pumps create pressure pulsations which are then transmitted to the tissue cavity. Such pressure pulsations are undesirable and the main aim of the present invention is to dampen such pressure pulsations.

A Safe Distending System:

An efficient distending system as explained in the previous paragraph need not also be a safe distending system. In this regard, the Inventors would like to highlight that if the cavity pressure rises above the prescribed safe limits excessive fluid intravasation may occur or the cavity may even burst. Fluid intravasation is a process by which the irrigation fluid enters into the patient's body system through the cavity walls and may cause significant danger to the patient's life including death. Thus a safe distending system is one which prevents or minimizes fluid intravasation and allows the surgeon to accurately know the instantaneous real time rate of fluid intravasation into the patient's body system.

No Prior Art is Absolutely Safe:

Many different types of uterine distending systems are known and are being commercially marketed by many different companies but none of these systems can be considered to be absolutely safe for the patient. This fact has been clearly stated in the 'Hysteroscopic Fluid Monitoring Guidelines proposed by the Ad Hoc Committee on Hysteroscopic Fluid Guidelines of the American Association of Gynecologic Laproscopists February 2000 (Loffler F D, Bradley L D, Brill A I et al: Hysteroscopic fluid monitoring guidelines. The journal of the Americal Association of Gynecologic Laproscopists 7(1): 167-168, 1994) where the authors clearly and explicitly state "fluid pumps for low-viscosity media are a convenience and do not guarantee safety". The present invention aims at providing a distending system which is both safer and more efficient in comparison to all the prior art systems.

Basic Physics of Cavity Distension:

Although, a person skilled in the art may know it, the Inventors would like to provide a brief description of the basic physics of cavity distension. Filling the tissue cavity with fluid enables distension of the same. Initially more fluid is pumped in than the amount which is extracted from the cavity and ultimately the inflow rate is fixed at a level where a somewhat desired cavity pressure and distension is achieved. It may be possible to accurately maintain the desired pressure and distension in the case of a rigid cavity, for example a cavity made of steel.

However, the body tissue cavities are not rigid because they are distensible and also have some element of elasticity. Thus a distended tissue cavity in its attempt to constantly revert back to its natural collapsed state reacts by exhibiting physiological contractions of the cavity wall which generally leads to variations in the cavity pressure which ultimately culminates in irregular movement excursions of the cavity walls. In a static system the said movement excursions may be so minute that they may even go unnoticed. However in a dynamic system such that being created during an endoscopic procedure, the said physiological cavity wall contractions may cause the cavity to expel out its entire fluid content thus leading to a surgically dangerous large magnitude movement excursion of the cavity wall. Because of these reasons it is extremely difficult to maintain the cavity pressure and cavity distension in a predictably stable fashion.

Further, the inflow tube, the out flow tube and the endoscope also invariably move and shake during surgery which leads to variations in fluid flow resistance which is also manifested in the form of variations in the cavity pressure. The cavity pressure variations occurring as a result of cavity wall contractions and the mechanical movement of the tubes and the endoscope tend to occur again even if they are corrected once because it is impossible to prevent the physiological cavity wall contractions and the mechanical movements of the irrigation circuit. Thus, the said cavity pressure variations shall continue to occur even after multiple repeated corrections.

Thus, till date the surgeon was only left with two options, either to ignore the said cavity pressure variations by not correcting them, or to externally and actively correct such pressure variations. The Inventors have noticed that any attempt to externally and actively correct the said cavity pressure variations leads to an undesirable turbulence inside the cavity and also tends to amplify the resultant movement excursions of the cavity walls. Thus there is a grave need to provide a system which can maintain an almost constant and stable cavity pressure even in the presence of the said physiological cavity contractions and the mechanical movements in the irrigation circuit.

Brief Description of an Endoscope

Prior to describing the basic layout of a continuous flow irrigation system the basic structure of an 'endoscope' needs to be described. Endoscope is a cylindrical tube having an outer diameter ranging between 3 to 9 mm approximately. A typical endoscope has four channels. One channel is meant to pass a fibereoptic telescope while endoscopic instruments are negotiated through a second instrument channel. A third channel also known as the inflow channel is used for pushing irrigation fluid into a tissue cavity, the proximal end of this channel ending in a metal adaptor known as the inflow port while the distal end of this inflow channel opens near the tip of the endoscope. The inflow port is connectable to an inflow tube which carries sterile irrigation fluid from a fluid source reservoir. A fourth channel also known as the out flow channel is meant for extracting waste fluid out of the cavity, the proximal end of this channel ending in a metal adaptor known as the outflow port while the distal end of this outflow channel opens near the tip of the endoscope. The outflow port is connectable with an outflow tube which transports the waste fluid from the cavity to a suitable waste fluid collecting reservoir. A set of fiber optic bundles contained inside the telescope transmit light energy produced by an external light source. This light energy illuminates the walls of the tissue cavity. The image thus formed is carried via a separate set of optical pathways again situated inside the telescope. A video camera attached to the eye piece of the telescope forms a clear endoscopic image of the cavity on a TV monitor. The endoscopic surgeon has to continuously look at the TV monitor all through the endoscopic procedure.

Basic Layout of a 'Continuous Flow Irrigation System:

Henceforth in this manuscript unless otherwise specified the term 'distension' shall be deemed to imply tissue cavity distension by 'continuous flow irrigation' only and the term 'cavity' unless specifically stated shall be deemed to refer to a 'body tissue cavity'. In a typical distension system a physiological non viscous liquid like 0.9% normal saline, 1.5% glycine, mannitol, ringer's lactate and 5% dextrose is stored in a sterile fluid source reservoir. A fluid supply tube connects the said fluid reservoir with the inlet end of a pump. The outlet end of the inflow pump is connected to the inflow port of an endoscope. When the inflow pump operates the fluid from the fluid source reservoir is sucked via the fluid supply tube and the inflow pump pushes this fluid into the tissue cavity via the said inflow tube. The pump operates by consuming certain amount of energy and as a result of this a positive fluid pressure is created inside the tissue cavity. An outflow tube extends between the outflow port and the inlet end of an outflow pump. When the outflow pump operates it actively extracts waste fluid from the cavity again at the expense of energy and this waste fluid is ultimately sent to a waste fluid reservoir via a tube which connects the outlet end of the outflow pump with the waste fluid reservoir. Alternatively the outflow pump may be missing and in such case the outflow tube directly carries the waste fluid from the cavity to the waste fluid reservoir and the energy for such act is supplied by gravity instead of the outflow pump. Also, the inflow pump may be missing and in such case the inflow tube directly supplies the irrigation fluid from a fluid source reservoir to the cavity. In such case the fluid source reservoir is hung at a suitable height above the patient and the said energy for cavity distension is derived from gravity instead of the inflow pump. A suitable pressure transducer is attached to the inflow tube, the outflow tube or directly to the cavity to measure the fluid pressure. A controller may be incorporated to regulate the system.

The Simplest Continuous Flow Irrigation System:

In its simplest form, a continuous flow irrigation system comprises a fluid reservoir bottle hung at a suitable height above the patient and an inflow tube connecting this fluid reservoir to a tissue cavity. An out flow tube is incorporated to remove fluid from the tissue cavity. In this system there is no pump and no transducer. In such a system fluid flows from the fluid source reservoir into the cavity and the required energy is supplied by gravity. The pressure developed inside the cavity can be increased or decreased by elevating or lowering the height of the fluid source reservoir. In such system the main limiting factor is the height of the room ceiling beyond which the fluid reservoir cannot be raised. This is a crude system having negligible practical importance and has been included only from the academic point of view. Also in such a system unlimited volume of irrigation fluid may enter into the patient's blood circulation. Thus such system is not suitable even from the patient safety point of view.

Basic Components of a Continuous Flow Irrigation System:

Like a motor car is made up of certain obvious components like engine, tyres and a steering wheel, a continuous flow distending system is made of components like pump, pressure transducer, flow regulating valve, rubber tubes and a controller. The pump may be a positive displacement pump like a peristaltic pump, piston pump or a gear pump or alternatively it may be a dynamic pump like a centrifugal pump. Further the said pump may be of a fixed RPM type which runs at fixed RPM all through the endoscopic procedure or the pump may be of a variable RPM type which operates at variable RPM during the endoscopic procedure. It is extremely important to note that fixed RPM pumps and variable RPM pumps are two separate mechanical entities in context with a cavity distending system because the fixed and variable RPM pumps impart different surgical efficiency and patient safety criteria to the distending system. The said pump may be attached on the inflow side only, on the outflow side only or both on the inflow and outflow side. Further if a pump is attached only on the inflow side the outflow tube may directly empty in a waste fluid reservoir at atmospheric pressure or a vacuum source may also be additionally attached. In some distending systems a flow controlling valve is attached on the outflow tube in order to regulate the cavity pressure. There may be a single pressure transducer attached to the inflow tube, the outflow tube or directly to the cavity. In some systems instead of one pressure transducer two pressure transducers may be used, one on the inflow tube and the other on the outflow tube.

Relvant references have been included in a PCT application filed by us in the past however three additional references are now being included. These references are U.S. Pat. No. 5,520,638, U.S. Pat. No. 4,902,277 and U.S. Pat. No. 5,578,012.

In U.S. Pat. No. 5,520,638 a variable speed peristaltic pump is used to push irrigation fluid into a tissue cavity. This patent is related to the 'Continuous Wave II Arthroscopy Pump' marketed by Arthrex. A chamber with volume is connected to the inflow tube and a collapsible bladder is contained within the bladder. The collapsible bladder has an open end connected with tubing to a pressure transducer. Once activated the pump begins to introduce fluid into the tissue cavity via the inflow tube and as pressure builds within the tissue cavity, fluid enters the chamber, and air in the chamber is compressed. The compressed air in the chamber compresses the bladder. Air pressure in the bladder is experienced by the pressure transducer. The pressure transducer feeds pressure information to a controller which regulates the RPM of the pump on the basis of a pressure feedback mechanism. Thus by the help of a pressure feedback mechanism the pressure inside a tissue cavity is maintained by fluctuating around a desired value. In this invention an important purpose of the said chamber is to dampen the pressure pulsations created by the peristaltic pump. Such pressure pulsations create turbulence inside the tissues cavity and are hence undesirable. The method of dampening the pressure pulsations as described in this U.S. Pat. No. 5,520,638 is not adequately efficient, especially at high pump RPM's. In the present invention a method shall be described by which the amplitude of the said pressure pulsations would be reduced to negligible magnitude even at a high pump RPM.

In U.S. Pat. No. 4,902,277 a pump is provided on the inflow side which pushes fluid into a tissue cavity while a positive displacement pump removes fluid from the cavity. This patent is related to 'FMS duo Fluid Management System' marketed by FMS Group. By the help of a pressure feedback mechanism the inflow pump is constantly increased or decreased thereby maintaining the cavity around a desired value. Thus by the help of a pressure feedback mechanism the pressure inside a tissue cavity is maintained by fluctuating around a desired value.

In U.S. Pat. No. 5,578,012 a centrifugal pump is deployed on the inflow side while no pump is deployed over the outflow side. This patent is related to the 'HydroFlex HD' pump marketed by DAVOL company. By the help of a pressure feedback mechanism the inflow pump is constantly increased or decreased thereby maintaining the cavity around a desired value. Thus by the help of a pressure feedback mechanism the pressure inside a tissue cavity is maintained by fluctuating around a desired value.

OBJECTS OF THE INVENTION

The overall objective of the invention is to provide a safe, efficient and turbulence free system for distending body tissue cavities for those endoscopic procedures which utilize continuous flow irrigation.

The main object of the invention is to minimize the amplitude of pressure pulsations, inside the tissue cavity, created by an outflow positive displacement pump to almost negligible levels, irrespective of the outflow pump RPM.

Another object of the invention is to minimize the frequency of pressure pulsations, inside the tissue cavity, created by an outflow positive displacement pump, without reducing the outflow pump RPM.

Yet another object of the present invention is to provide a system for distending tissue cavities using which it being possible to create and maintain a desired precise cavity pressure for a desired precise rate at which fluid may be allowed to flow through the cavity, for any length of time.

Still another object of the present invention is to provide a system for distending tissue cavities using which it being possible to achieve a predictably constant clear endoscopic vision throughout the endoscopic procedure.

Yet another object of the present invention is to provide a system for distending tissue cavities using which it being possible to achieve a predictably stable mechanical cavity distension throughout the endoscopic procedure.

One more object of the present invention is to provide a system for distending tissue cavities using which it being possible to predictably maintain the cavity pressure at any desired precise value despite physiological contractions of the cavity wall.

One another object of the present invention is to provide a system for distending tissue cavities using which it being possible to constantly, accurately and reliably determine the instantaneous real time rate of fluid intravasation into the patient's body by using hot wire anemometer type of fluid rate sensors.

A further more object of the present invention is to provide a system for distending tissue cavities using which it being possible to maintain any desired precise and high cavity pressure without increasing the 'maximum possible fluid intravasation rate'.

Another object of the present invention is to provide a system for distending tissue cavities using which it being possible to measure the actual cavity pressure, in an accurate, reliable and simple manner, by using a pressure transducer located far away from the cavity in the up stream portion of the inflow tube.

Yet another object of the present invention is to provide a system for distending tissue cavities using which it being possible to make the pressure inside the body cavity and the flow rate of the fluid passing through the body cavity absolutely independent of each other such that the value of any may be altered without affecting the value of the other.

One more object of the present invention is to provide a system for distending tissue cavities using which it being possible for the surgeon to have a fairly accurate assessment of the total volume of the irrigation fluid which would be required to complete the entire endoscopic procedure.

SUMMARY OF THE INVENTION

The main aim of the present invention is to minimize fluid turbulence inside tissue a cavity during endoscopic procedures. The present invention is a safe and an efficient system for distending body tissue cavities for those endoscopic procedures which utilize continuous flow irrigation. In the present invention the amplitude of tissue cavity pressure fluctuations caused by a positive displacement outflow pump can be minimized to almost negligible levels. The pressure pulse frequenct can also be reduced for the same cavity outflow rate. The present invention is a system of creating and maintaining a desired positive pressure inside a body tissue cavity through which fluid can be made to flow at a desired fixed flow rate. Alternatively the present invention may be considered as a system of creating cavity fluid pressure which is absolutely independent of the cavity outflow rate. The present invention comprises of a dynamic pump like a centrifugal pump on the inflow side and a positive displacement pump such as a peristaltic on the outflow side which can work simultaneously, for indefinite time, at fixed RPM's to create and maintain a desired precise cavity pressure for a desired cavity outflow rate. Also in the proposed invention the changes in the tissue cavity pressure are not actively corrected as is done in many prior art systems. Also the same system can be used for multiple endoscopic procedures which utilize continuous flow irrigation.

DETAILED DESCRIPTION OF INVENTION

Figure 1:
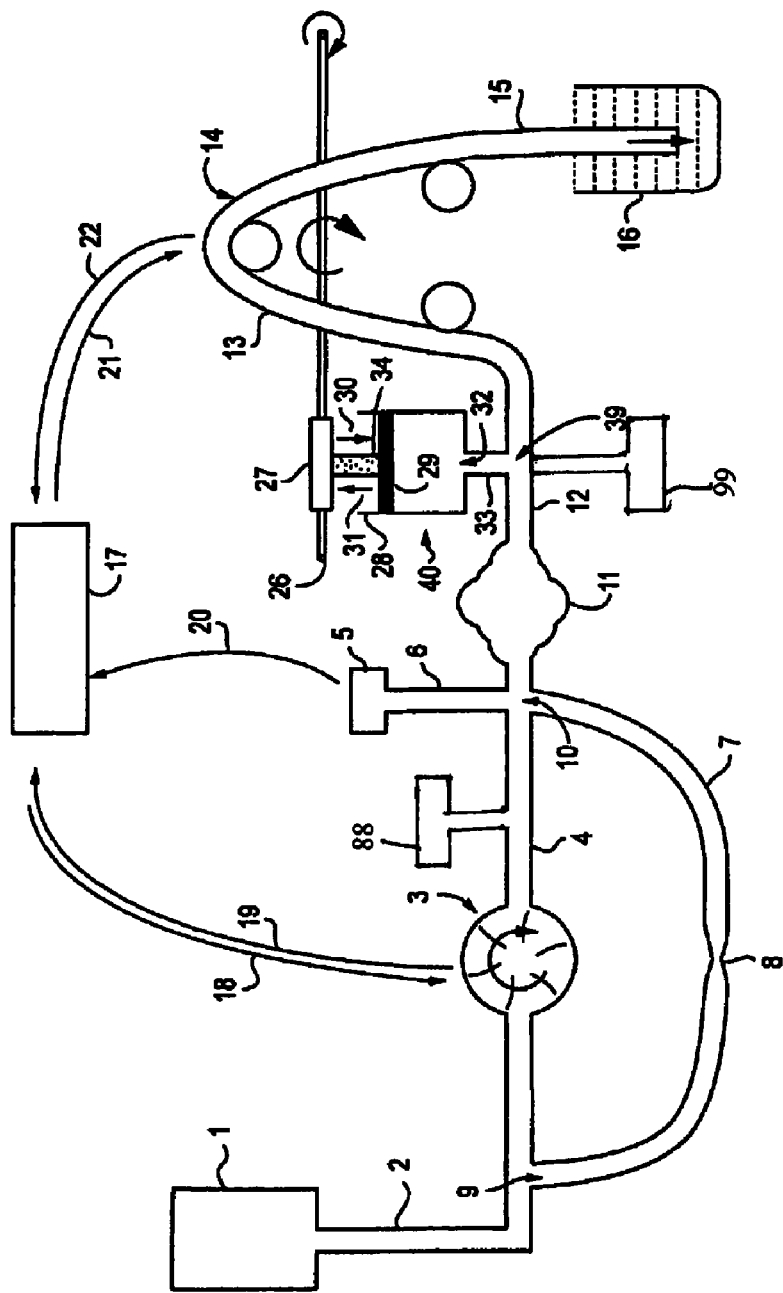
FIG. 1 shows the main block diagram of the invention along with a 'pressure pulse dampening system' and the controller.

Accordingly, the present invention provides a system for distending body tissue cavities of subjects by continuous flow irrigation during endoscopic procedures the said system comprising:
a fluid source reservoir containing a non viscous physiologic fluid meant for cavity distension;
a fluid delivery tube connecting the fluid source reservoir to an inlet end of a inflow dynamic pump and an outlet end of the said pump being connectable to an inflow port of an endoscope instrument through an inflow tube for pumping the fluid at a controlled flow rate into the cavity, the rate at which the fluid from the inflow tube enters into the tissue cavity being termed as the cavity inflow rate;
an outflow port of the endoscope being connectable to an inlet end of a variable speed positive displacement outflow pump through a outflow tube for removing the fluid from the cavity at a controlled flow rate, the flow rate of the said outflow pump being termed as the cavity outflow rate,
an outflow pressure pulsation dampening means connected to the outflow tube for dampening the pressure pulsations inside the cavity caused by the positive displacement outflow pump;
an outlet end of the outflow pump being connected to a waste fluid collecting container via a waste fluid carrying tube, and characterized in that a housing tube having a controllable constriction site is being provided between the fluid source reservoir and the inflow tube such that the same by-passes the inflow pump; wherein housing tube provides a route for any excess fluid being pumped by the inflow pump to bypass the inflow pump and go back to the fluid supply tube or the fluid source reservoir, thereby minimizing turbulence inside the cavity and maintaining the cavity pressure at a stable value despite physiological contractions of the cavity wall.

In an embodiment of the present invention, the fluid source reservoir containing the non-viscous physiologic fluid is maintained at atmospheric pressure or at a pressure greater than the atmospheric pressure.

In another embodiment of the present invention, wherein the fluid source reservoir is situated at the same horizontal level as the inflow dynamic pump or is situated at an elevated location with respect to the inflow dynamic pump or is situated at a lower horizontal level with respect to the inflow dynamic pump.

In yet another embodiment of the present invention, wherein if the fluid source reservoir is located at a level lower than the inflow dynamic, the fluid delivery tube is provided with a foot valve at its proximal end.

In still another embodiment of the present invention, a proximal open end of the fluid delivery tube is connected to the fluid source reservoir and a distal end of the tube is connected to the inlet end of the centrifugal pump.

In one more embodiment of the present invention, a proximal end of the inflow tube is connected to the outlet end of the centrifugal pump and a distal end of the inflow tube being connectable to the inflow port of the endoscope instrument.

In one another embodiment of the present invention, the housing tube is releasably provided between the fluid source reservoir and the inflow tube to enable replacement of the housing tube with yet another housing tube having a different diameter at the constriction site to suit the operational need of the endoscopic procedure.

In one further embodiment of the present invention, a proximal end of the housing tube is connected to the fluid delivery tube near its distal end close to the inlet end of the centrifugal pump.

In a further embodiment of the present invention, a distal end of the housing tube is connected to the inflow tube near its proximal end close to the outlet end of the centrifugal pump.

In a further more embodiment of the present invention, the housing tube is provided with a clamping means at the constriction site to enable the user to vary the diameter of the housing tube at the constriction site to suit the operational needs of endoscopic procedures.

In an embodiment of the present invention, the diameter of the housing tube at the constriction site is in the range of 0.001 mm to a maximum value which is less than the overall diameter of the rest of the housing tube In another embodiment of the present invention, the diameter of the housing tube at the constriction site is in the range of 0.01 to 2.5 mm.

In yet another embodiment, the system of the present invention further comprises a fluid inflow rate sensor connected to the inflow tube for measuring the cavity inflow rate.

In still another embodiment of the present invention, the fluid inflow rate sensor is located between the inlet port of the endoscope and the location where the housing tube is connected to the fluid flow tube.

In one more embodiment of the present invention, a proximal end of the outflow tube being connectable to the outlet port of the endoscope instrument and a distal end of the outflow tube is connected to an inlet end of the variable speed positive displacement outflow pump.

In one another embodiment, the system of the present invention further comprises a housing tube having a variable size constriction site being provided between the outflow tube and the waste fluid reservoir.

In one further embodiment, the system of the present invention further comprises a fluid outflow rate sensor connected between the proximal end of the outflow tube and the inlet end of the variable speed positive displacement outflow pump for measuring the fluid outflow rate.

In a further embodiment of the present invention, the fluid outflow rate sensor is located between the outlet port of the endoscope and the location where the housing tube is connected to the outflow tube.

In a further more embodiment of the present invention, the fluid inflow or outflow rate sensors consist of a heating coil in physical contact with a metal plate for heating the same and a temperature sensor placed in contact with the metal plate for measuring the temperature of the said metal plate, the temperature of the metal plate being a function of the fluid flow rate.

In an embodiment of the present invention, the fluid rate sensor is a hot wire anemometer.

In another embodiment of the present invention, instantaneous real time rate of intravasation is determined by connecting the inflow and the outflow flow rate sensors to a micro-controller.

In yet another embodiment of the present invention, the variable speed positive displacement outflow pump is selected from the group comprising peristaltic pump, piston pump, gear pump, diaphragm pump and plunger pump.

In still another embodiment of the present invention, the variable speed positive displacement outflow pump is a peristaltic pump.

In a further embodiment of the present invention, the outlet end of the variable speed positive displacement outflow pump is connected to the waste fluid collecting container through a waste fluid carrying tube.

In one more embodiment, the system of the present invention further comprises an outflow pressure transducer connected to the outflow tube for sensing the outflow pressure.

In one another embodiment, the system of the present invention further comprises a micro-controller means electrically coupled to the inflow pressure transducer, the outflow pressure transducer, the inflow pump and the outflow pump for regulating the operation of the inflow and the outflow pumps.

In one further embodiment of the present invention, the housing tube is provided with an electromechanical device, a solenoid, to enable the micro-controller to vary the diameter of the constriction site.

In a further more embodiment of the present invention, the fluid supply tube, the inflow tube, the outflow tube and the waste fluid carrying tube are flexible, disposable and are made of polymeric material.

In an embodiment of the present invention, the pressure dampening means comprises a single outlet syringe mechanism, a piston of the same being coupled synchronously to the positive displacement outflow pump through coupling means and the single outlet end of the said syringe mechanism being connected to the outflow tube.

In another embodiment of the present invention, the variable speed outflow peristaltic pump is provided with 1 to 5 peristaltic pump tubes connected in parallel between the inflow and the outflow end of the peristaltic pump for reducing the frequency of pulsations of in the pressure, the said peristaltic pump tubes being connected to each other at the inflow and the outflow end of the peristaltic pump.

The proposed invention is described hereafter with reference to the accompanying drawings in order to clearly explain and illustrate the system and the working of the system. It is respectfully submitted the scope of the invention should not be limited by the description being provided hereafter.

The system of the present invention is a unique system for distending body tissue cavities in endoscopic procedures. In the proposed invention a body tissue cavity is distended by continuous flow irrigation in such a manner that the amplitude of the pressure pulsations created by the positive displacement pumps can be reduced to a negligible value. In the proposed invention a method of reducing of the said pulsations has also been described. Also the cavity pressure is absolutely independent of the cavity outflow rate, such the both, the cavity pressure and the outflow rate, may be independently altered without varying the value of the other parameter.

Figure 2:
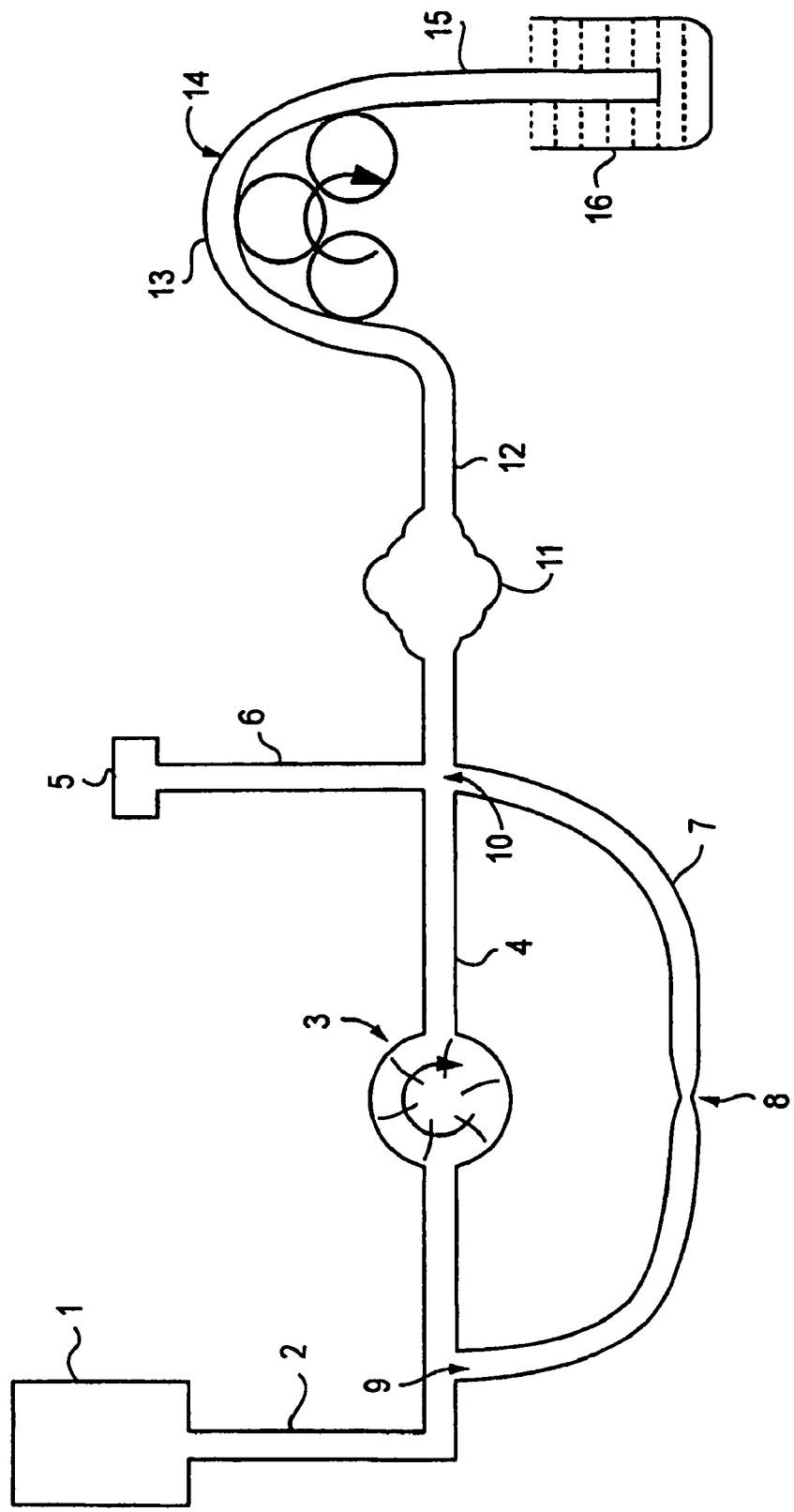
FIG. 2 shows the block diagram of the invention without the 'pressure pulse dampening system' and without the controller.

FIG. 1 shows the main diagram of the invention. In FIG. 1 the inflow and the outflow 'pressure pulse dampening systems', have been shown clearly. However in order understand the invention in a simpler manner, first the basic invention without the 'pressure pulse dampening system' shall be discussed. The basic schematic diagram of the invention is shown in FIG. 2. FIG. 2 is similar to FIG. 1 except that in FIG. 2 the 'pressure pulse dampening system' has not been included. The two pumps 3 and 14 operate simultaneously in order to distend a tissue cavity in such a manner that the cavity pressure is totally independent of the cavity outflow rate.

A basic schematic diagram of the invention is shown in FIG. 2. A fluid source container 1 containing a physiological fluid such as normal saline or 1.5% glycine at atmospheric pressure and is hung at a suitable height above the inflow pump 3, the inflow pump preferably being a centrifugal pump. The fluid source container 1 is connected to the inlet end of a centrifugal pump 3 via a fluid delivery tube 2. An inflow tube 4 which carries the pressurized irrigation fluid to the tissue cavity 11 extends between the outlet end of the centrifugal pump and the inlet of the cavity or the inflow port of an endoscope. Similarly an outflow tube 12 extends between the outflow port of the endoscope and the inlet end of a positive displacement pump 14, preferably a peristaltic pump. The tubing of the peristaltic pump 14 has been labeled as 13 and such tube consists of a suitable resilient plastic material which can be efficiently compressed by the rollers of the peristaltic pump 14. A waste fluid carrying tube 15 connected to the outlet end of the peristaltic pump 14 drains into a waste fluid collecting container 16. The direction of rotation of the two pumps is represented by curved arrows. A pressure transducer 5 is attached at one of tube 6 while the other end of tube 6 is connected anywhere on inflow tube 4. For practical convenience it is desirable that the said other end of tube 6 be connected in the up stream part of the inflow tube 4 such as at a square junction 10. The pressure transducer 5 measures the fluid pressure via a column of liquid or air present in the lumen of tube 6. The fluid pressure as measured by the pressure transducer shall be referred to as P. In this manuscript the term 'P' shall frequently be used to refer to the actual pressure inside the tissue cavity but in absolute terms P is the pressure sensed by the transducer 5 at point 10. The pressure transducer 5 may also be in the form of a membrane diaphragm incorporated in the wall of the inflow tube 4 such that this membrane diaphragm is in direct contact with the fluid contained in the inflow tube 4, such that the linear movement excursions of the said membrane are interpreted as pressure of the fluid inside the inflow tube 4. Such type of pressure sensor being directly incorporated in the wall of the inflow tube 4 senses the fluid pressure without the intervention of tube 6. The basic purpose of the transducer is to measure the fluid pressure inside the inflow tube 4, such as at point 10, thus the mechanical construction of such a pressure transducer is not important as long as the fluid pressure is measured in a reliable and accurate manner. For the sake of simplicity the existence of tube 6 shall be continued to be considered in the rest of the manuscript. A constriction site housing tube 7 extends between the 'T junction' 9 situated at the inlet end of the pump 3 and the 'square junction' 10 situated at the outlet end of the pump 5. The 'T' junction 9 is thus a symbolic reference to a point where one end the constriction site housing tube 7 is connected to the fluid delivery tube 2. Similarly the said square junction 10 is also a symbolic reference to a point where the other end of tube 7 joins the inflow tube 4. Tube 7 has a constriction point 8 which can be located anywhere along its length. Such constriction point refers to a point where the inner diameter of the lumen of tube 7 is reduced in comparison to the lumen of the rest of the tube 7. Such constriction may be a permanent constriction in the lumen of tube 7 or it may be a variable constriction whose diameter may be increased or decreased as desired. The two pumps 3 and 14 operate simultaneously in order to distend the tissue cavity 11 in such a manner that the cavity pressure is totally independent of the cavity outflow rate. The two pumps can maintain a predictably precise stable cavity pressure for indefinite time by working simultaneously at constant rotational speeds. Pump 3 pushes fluid into the cavity 11 and while pump 14 simultaneously extracts fluid out of the cavity 11. The rollers of the outflow peristaltic pump 14 continuously compress and roll over the entire length of tube 13 thus displacing fluid. This curved arrow denotes the direction in which the rotors of the peristaltic pump 14 rotate. The peristaltic pump 14 being attached to the outflow side actively extracts fluid out of the tissue cavity 11 via the out flow tube 12. The outlet end of the pump 14 is connected to a waste fluid carrying tube 15 which opens into a waste fluid collecting reservoir 16 at atmospheric pressure. Also the rollers of the peristaltic pumps 14 should press adequately over tube 13 in such a manner that there is no leak via these tubes when the pump is stationary. It is assumed that there is no abnormal leak of fluid anywhere in the irrigation system, for example leak via a accidental hole made in any irrigation tube or a fluid leak which might occur if the endoscope loosely enters into the tissue cavity, for example in hysteroscopic surgery fluid leaks by the sides of the endoscope if the cervix is over dilated. It is also assumed that all the components shown in FIG. 2 except the fluid source container 1 and the fluid deliver tube 2 are placed at the same horizontal height with respect to the ground. As already mentioned that the fluid source reservoir 1 is placed at an elevated position with respect to centrifugal pump 3, however the reservoir 1 can also be placed at the same level with respect to the centrifugal pump 3 or at a location which is lower than the pump 3. However if the reservoir 1 is placed lower than the centrifugal pump 3 then a foot valve may need to be installed in the proximal open end of the fluid delivery tube 2.

Figure 3:
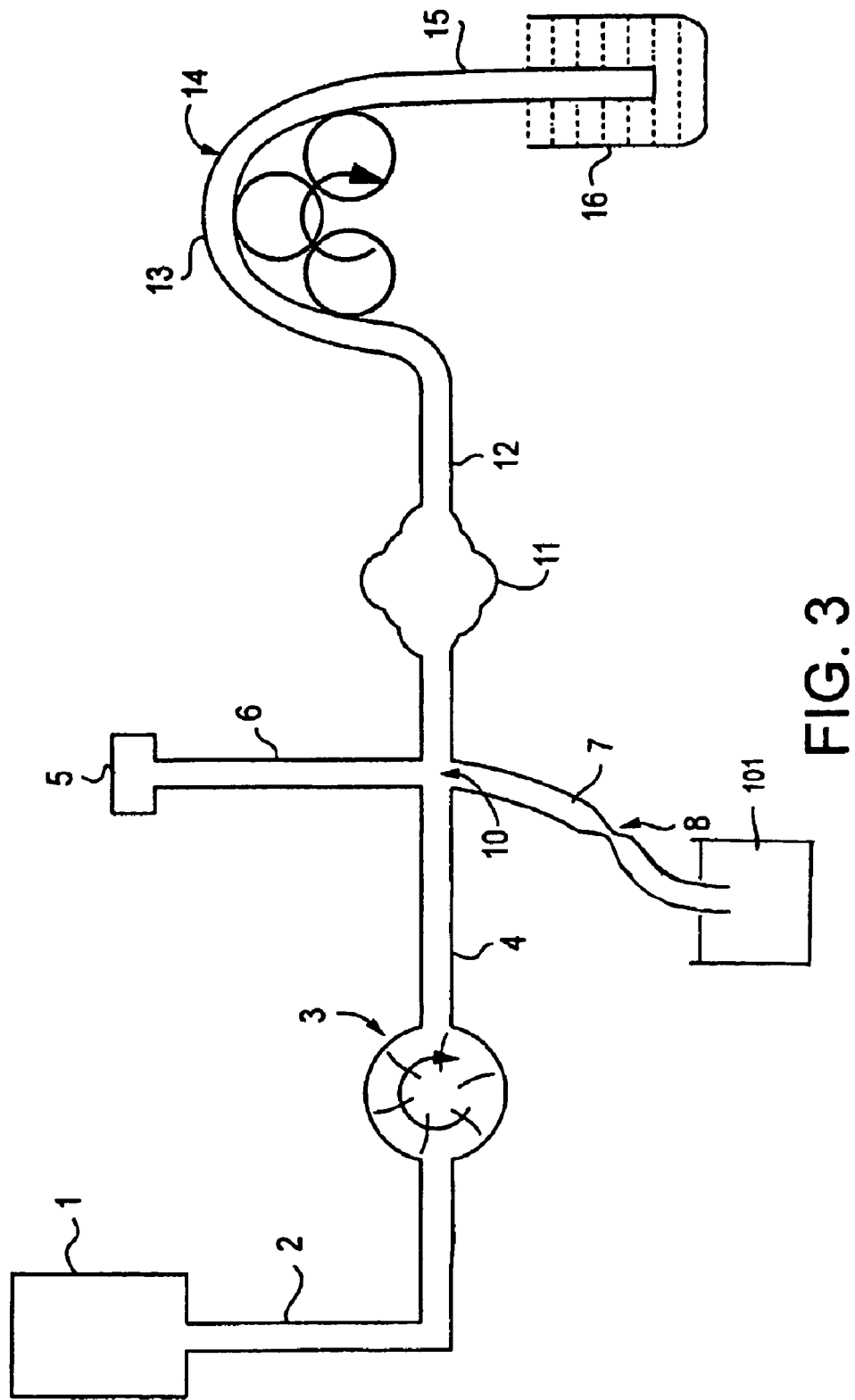
FIG. 3 is similar to FIG. 2 except that the housing tube 7 empties into an additional container at atmospheric pressure.

As shown in FIG. 3 one end of the constriction site housing tube 7 instead of being connected with tube 2 at the 'T' junction 9 can also drain directly into a suitable container 101 other than the reservoir 1. One end of the constriction site housing tube 7 instead of being connected with tube 2 at the 'T' junction 9 can also drain directly into the fluid source reservoir 1, such provision would also conserve costly irrigation fluid, however such provision has also not been shown FIG. 3 in order to keep the drawing simple. However the system wherein one end of tube 7 joins the T junction 9 is considered most practical from the surgical point of view and shall be considered in the rest of the manuscript.

Figure 4:
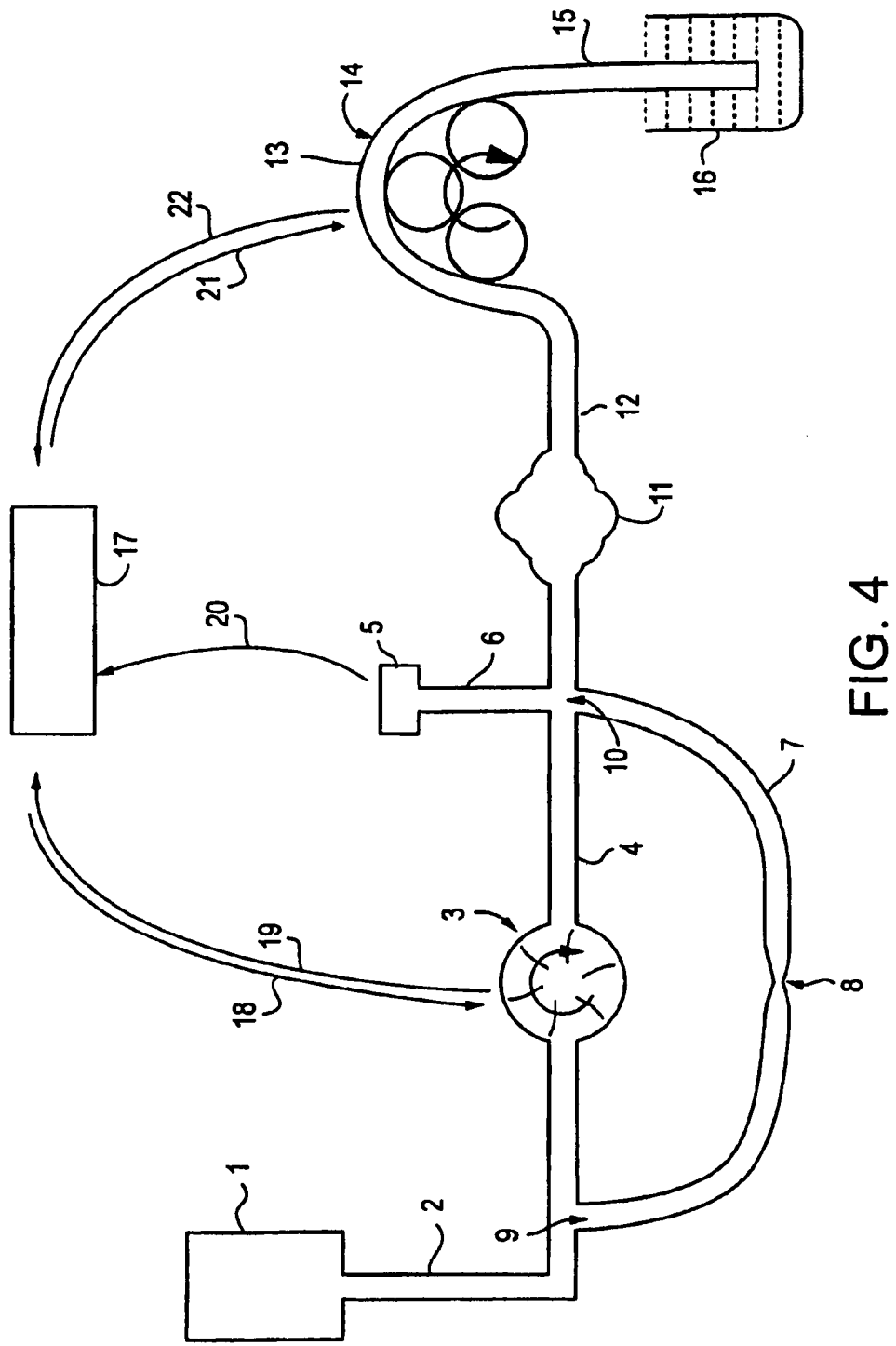
FIG. 4 is similar to FIG. 2 except that a controller has been included.
Figure 5:
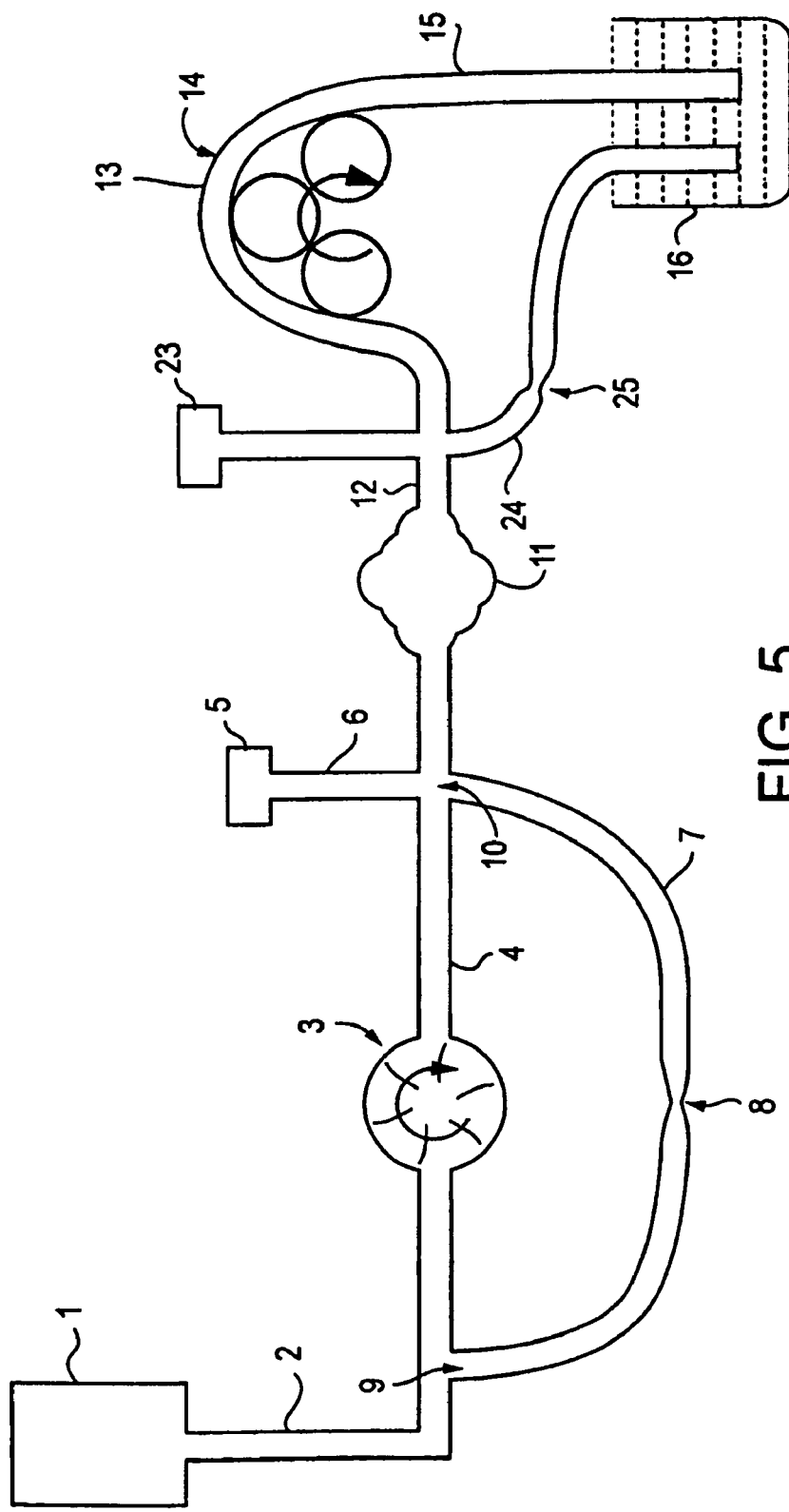
FIG. 5 is similar to FIG. 2 except that an optional housing tube 24 and an optional pressure transducer 23 have been included.

Also, a constriction site housing tube similar to tube 7 labeled as 24 can be attached to the outflow tube 12 as shown in FIG. 5. In the said tube 24 the said constriction site is labeled as 25. Such tube can serve a number of purposes. Tube 24 can be utilized for relatively faster evacuation of air bubbles from the cavity. The said bubbles are invariably created inside the cavity as a result of electrosurgical cutting and coagulation or they may enter the cavity while the endoscope is being introduced into the cavity. Such bubbles cause extreme nuisance for the surgeon because they obscure vision and thus the surgical time may be greatly increased. In routine surgery the surgeon moves the tip of the resectoscope near the bubble and the bubble is sucked out of the cavity by the process of continuous flow irrigation. However in certain situations it may not be possible to bring the tip of the resectoscope near the bubble, one such situation is when bubbles accumulate inside a very deep cornuae associated with a long septum, the diameter of the cornuae being less than the outer diameter of the resectoscope. In such a situation the tubal opening situated at the center of the cornuae can only be visualized after evacuating such bubbles from the cavity. In such situation the bubbles can be quickly evacuated without moving the tip of the resectoscope near the bubbles by simply opening the constriction 25 in the tube 24. However such maneuver tends to completely collapse the cavity. Thus if the resctoscope tip is only moderately away from the bubbles the constriction is opened only partially so that the bubbles are sucked out and the cavity collapses by a relatively smaller magnitude. In place of the adjustable constriction site 25 a pressure release safety valve may be incorporated as a safety feature, however it is more beneficial to install such pressure safety valve in the inflow circuit. The tube 24 may also be used for quickly flushing air bubbles from the irrigation tubes by fully opening the constriction site 25 for a few minutes or seconds. The tube 24 may also be used for any other purpose as deemed fit by the surgeon. However the said tube 24 has intentionally not been included in FIGS. 1 to 4 because by including the tube 24 in these figures it would have become very difficult to explain the basic fundamentals principals of the invention. However tube 24 is a very beneficial component and is thus recommended to be incorporated in the system of the proposed invention. The opening and closing of the constriction site 25 can also be regulated manually to help in various special advanced endoscopic applications. Incorporation of tube 24 with a variable constriction site 25 can help in reducing the substantially high amplitude pressure variations inside the cavity caused by abnormally large cavity wall contractions, but such phenomenon is only rarely encountered. Also an additional pressure transducer 23 may also be attached on the out flow tube 12, if desired, as shown in FIG. 5. However the said pressure transducer 23 has intentionally not been included in the main block diagrams of the invention because by doing so it would have become difficult to explain the basic principals related to the invention.

After activating the pump 3 if the constriction site 8 is fully occluded a column of fluid is immediately sucked withdrawn from the fluid source container via the fluid supply tube 2 and this starts filling the cavity 11. Now if the inflow tube is blocked by closing the inflow port fluid starts accumulating in the proximal parts of tubes 6 and 7. As the fluid fills in tube 6 it pushes a column of air distal to the fluid column created in tube 6 and the pressure of this compressed air column is sensed by the pressure transducer 5. The fluid pressure and the pressure of the said compressed air column are same thus the pressure transducer 5 actually senses the fluid pressure. If tube 7 continues to remain fully occluded at the constriction site 8, the fluid continues to accumulate inside tube 6, the distally blocked inflow tube 4 and in that part of tube 7 which lies between point 10 and the constriction site 8, and the pressure transducer 5 thus displays a rising fluid pressure until the pressure becomes equal to the pressure head of the centrifugal pump. The moment the block at the constriction site 8 is partially released the fluid escapes in the form of a jet through the partially open constriction opening 8 in the direction of point 9. With the constriction opening 8 being only partially blocked, if the pump 3 continues to rotate at a constant rotational speed the fluid pressure ultimately gets stabilized at a fixed value provided the internal diameter of the constriction site 8 is not further varied. The diameter D of the constriction site 8 ranges from a minimum non-zero value to a maximum value which is less than the overall diameter of the rest of the housing tube, that is between a minimum value when the constriction site 8 is fully occluded, to a maximum value which is less than the inner diameter of tube 7. Henceforth in this manuscript the inner diameter of the constriction site 8 shall be deemed to be fixed at some predetermined value D, unless otherwise stated.

Referring to FIG. 2 it shall be first described as to how the system of the proposed invention can be used mechanically, that is without a controller. The peristaltic pumps 3 and 14 can be made to work at any fixed rotational speeds. The fluid flow rate of the outflow peristaltic pump 14 being directly proportional to the RPM of the outflow pump 14. Henceforth the inflow pump rotations shall be termed as 'RPM.inflow'. The flow rate of the inflow centrifugal pump is related to the pressure P in a hyperbolic manner The fluid flow rate of pump 14 shall henceforth be denoted by R2 and shall be termed as the 'outflow rate'. The fluid flow rate of pump 3 shall be denoted by R1 and shall be termed as the 'inflow rate' Here it is to be noted that the term 'inflow rate' R1 is not the true inflow rate for the cavity 11, as might be suggested by the literary meaning of the term 'inflow' because R1 is not the actual rate at which fluid flows into the cavity 11 because some fluid also constantly escapes through the constriction site opening 8. Henceforth in the entire manuscript the term 'inflow rate' shall only be referred to the flow rate or the volume displacement rate of the inflow pump 3 unless specifically mentioned. However the term 'outflow rate' R2 does correspond to the literary meaning of the term 'outflow' because R2 is equal to the rate at which fluid flows out of the cavity 11. The surgeon initially decides an out flow rate R2 by selecting a suitable rotational speed for pump 14. Next, both pumps are activated and the diameter D of the constriction site is increased or decreased in order to achieve a desired pressure inside the tissue cavity 11. Once a desired pressure is achieved inside the tissue cavity the diameter of the constriction site 8 is not altered any further and is fixed. The diameter of the constrictions site at this stage is termed as "D". The constriction site may also be a plastic or metal piece which has a hole in the centre such that the diameter of the hole is permanently fixed at some value D. If a constriction 8 has a permanently fixed diameter then only the flow rates of pumps 14 and the 'RPM.inflow' of pump 3 have to be set in order to operate the system at a desired cavity pressure.

The Inventors here would like to discuss about the importance of incorporating the housing tube 7 with the constriction site and the non-obvious advantages provided by the housing tube 7 with the constriction site.

As mentioned earlier, till date the surgeons were left with only two options, either to ignore the cavity pressure variations by not correcting them, or to externally and actively correct such pressure variations. To externally and actively correct the variations in the cavity pressure, controller was incorporated and the working of the pumps were essentially controlled by the controller. Incorporation of the controller controlling the operation of the pumps did not provide any benefit. The controllers used to activate the controlling action after the variations in the cavity pressure had subdued. Thus, the controlling action initiated by the controller instead of benefiting the surgeon leads to an undesirable turbulence inside the cavity and also tends to amplify the resultant movement excursions of the cavity walls.

The Inventors have noticed that if the controller continuously controls the operations of the pumps (either on the inflow side or on the outflow side), the cavity pressure continuously fluctuates around a preset value and it is not at all possible to attain a constant value. The Inventors believe that the controller provides proper corrective action (by continuously controlling the operations of the pumps) only if the fluctuations in the cavity pressure are gradual and not highly instantaneous. That is, if the quantitative rise or fall in the cavity pressure is over long time period, the controller would be able to provide proper corrective action. As the time period to detect variation in the cavity pressure and commence corrective action is ideally in the range of 2 to 4 seconds, if the quantitative rise or fall in the cavity pressure is over very short time period, the suggested mechanism of providing a controller will be unsuitable. Under such instances, instead of providing any corrective action, the controller destabilizes the system and induces additional pressure fluctuations inside the cavity (because of commencing a corrective action at a delayed stage). Thus it takes very long time period for the system to once again get stabilized.

The Inventors have surprisingly found that by incorporating a housing tube provided with a constriction site at the inflow side as described above, inherently and passively corrects the pressure variations due to physiological cavity wall contractions and the mechanical movement of the tubes and the endoscope and also limits the variation in the size of the cavity. The applicants would like to highlight that it is important to control both the variations in the pressure inside the cavity and the changes in the size of the distended cavity. Large variations in the pressure inside the cavity or the size of the cavity are detrimental to the surgical procedure. In all the prior art systems attempts were made to either control the variations in the pressure or the variations in the cavity size. But none of the prior art document the need to control both the cavity pressure variations and the cavity size variations and hence failed to provide a safe and ideal system. During the contraction of the cavity, a minute quantity of the fluid is pushed out of the cavity. If during this stage the system does not provide a way for releasing the fluid being pushed out, the instantaneous pressure inside the cavity would rise. On the other hand, if the amount of fluid being pushed out of the cavity is not checked and controlled, the changes in the size of the distended cavity are very high. The incorporation of the housing tube having the constriction site for the first time in the present system controls both the variations in the pressure inside the cavity and the changes in the size of the distended cavity. The housing tube having the constrictions site provides a by-pass route for the fluid being pushed out of the cavity to go back to the fluid supply tube or the fluid source reservoir. This avoids the instantaneous pressure surge inside the cavity. The size of the diameter at the constriction automatically controls the amount of fluid passing through the housing tube, thereby controlling the amount of fluid being pushed out of the cavity. Inclusion of the housing tube with the constriction site therefore minimizes the instantaneous variations in the size of the distended cavity.

Alternatively if the cavity expands a suitable volume of fluid is sucked into the cavity from the irrigation circuit, such as from the region of point 10, and this is accompanied by a corresponding transient decrease in the flow rate at which fluid which fluid is escaping via the constriction site 8 in the direction of point 9 but if the magnitude of the said physiological expansion is more fluid may even be sucked into the cavity via the constriction site 8. This implies that the constriction site 8 is helping in maintaining a stable cavity pressure despite physiological cavity wall contractions by suitably varying the magnitude, and occasionally if required even the direction, of an imaginary fluid flow vector passing through the constriction site 8.

Cavity Pressure or the Outflow Rate, Both can be Altered Independently without Varying the Value of the Other Parameter:

Referring again to FIG. 3 an hypothetical endoscopic procedure is being considered where surgery is being performed at an outflow rate R2 and the inflow pump is rotating at 'RPM.inflow' and the constriction 8 diameter being been fixed at some value D and a resultant cavity pressure P being created and maintained. In such hypothetical situation as long as R2 and 'RPM.inflow' are not altered the cavity pressure P remains predictably constant throughout surgery resulting in a predictably stable mechanical distension of the tissue cavity walls which culminates in constant clear visualization throughout the endoscopic procedure. If in the said hypothetical procedure the cavity pressure needs to be increased without altering the out flow rate R2 then all that is needed is to start increasing the value of 'RPM.inflow' and stop doing so when the desired higher cavity pressure is achieved. Similarly if the cavity pressure needs to be decreased without altering the out flow rate R2 then 'RPM.inflow' is decreased till the desired lower cavity pressure is attained. In the said hypothetical endoscopic procedure if the outflow rate R2 needs to be increased without altering the cavity pressure P then the value of R2 is increased by the desired magnitude but simultaneously the value of 'RPM.inflow' is also increased by a suitable magnitude. Similarly, if the outflow rate R2 needs to be decreased without altering the cavity pressure P then the value of R2 is decreased by the desired magnitude but simultaneously the value of 'RPM.inflow' is also decreased by a suitable magnitude. Thus in the proposed invention the cavity pressure and the outflow rate both can be altered absolutely independent of each other without affecting the value of the other parameter.

Mechanical Version of the Invention

The mechanical version of the invention shown in FIG. 3 can be used practically in endoscopic surgeries but it requires a skilled operator having a detailed knowledge of the physical principals involved in cavity distension, which may not be always possible. Also the mechanical version has many practical limitations. This mechanical version of the invention has been discussed only in order to explain more clearly the physical principals associated with the main invention shown in FIG. 1.

Controller Based Version of the Invention

Referring to FIG. 4, this figure shows a basic schematic diagram of the invention. FIG. 4 is similar to FIG. 2 except that in FIG. 4 a controller system has also been included. A tachometer, not shown in the diagrams, is coupled to each pump and sends information regarding the pump rotation speed to the controller 17 via wires 19 and 22. In context with the outflow peristaltic pump the pump flow rates being proportional to the pump rotation speed the tachometer signal always conveys flow rate related information to the controller. While in context with pump 3 the tachometer signal only conveys RPM related information. The controller also regulates the rotation speed of the two pumps via electrical signals sent through wires 18 and 21. The pressure transducer 5 conveys the pressure signal to the controller via wires 20. On the basis of a pressure feed back signal received from the pressure transducer 5 the controller regulates the rotational speed of the inflow pump 3. The outflow pump 14 works at fixed RPM's thus fixed outflow rates, however if the surgeon desires the outflow rate can be varied to another fixed value via suitable electrical signals sent by the controller 17 via wires 21. A provision exists by which desired values for P and R2 can be fed into the controller and the values RPM.inflow, R2 and P can be continuously displayed via suitable display means incorporated in the controller.

Method of Operating the Controller Based Version of the Invention

Again referring to FIG. 4, in context with the present invention at the start of surgery the surgeon initially selects suitable values for cavity pressure P and outflow rate R2. The said desired values of P and R2 are fed into the controller via suitable input means incorporated in the controller. The diameter D at the constriction site 8 remains fixed at some pre selected value. The diameter of the constriction site 8 is so chosen that it suits the operational needs of the endoscopic procedure. When the system shown in FIG. 4 is operated the controller 17 instructs the outflow pump 14 via wires 21 to continuously extract fluid out of the body cavity 11 at a desired fixed outflow rate R2. Thus all through the surgery the outflow rate remains fixed at R2 irrespective of any internal or external factors unless intentionally changed by the surgeon. The cavity pressure is sensed by the pressure transducer 5 and a corresponding pressure feedback signal is sent to the controller via wires 20 on the basis of which the controller regulates the 'RPM.inflow' via wires 18. After the system is made operational the controller 17 gradually increases 'RPM.inflow' up to the point where the desired preset cavity pressure P is achieved. Let the value of the 'RPM.inflow' at which the desired cavity pressure is achieved be termed as 'RPM.final'. It is obvious that the value 'RPM.final' is actually determined by the controller by a pressure feed back mechanism and such determination of the value 'RPM.final' is based on the preset values of R2 and P. The controller is so programmed that once the value 'RPM.final' is achieved and is maintained for a desired minimum time interval, for example 10 seconds, after which the controller releases the inflow pump 3 from its pressure feedback control mechanism and allow the inflow pump 3 to operate on its own at 'RPM.final' which was determined by the controller. In this manner the two pumps continue to work at fixed RPM's to maintain a desired stable cavity pressure. The controller is also programmed that in case the cavity pressure subsequently alters, for example due to intravasation, by a desired minimum preset magnitude and for a desired minimum time, which may hypothetically be 10 seconds, the inflow pump 3 again comes under the pressure feedback control of the controller and a new value of 'RPM.final' is determined by the controller after which the inflow pump 3 is again allowed to be operated without the pressure feedback mechanism at the newly determined value 'RPM.final'. Such sequence of events continue to occur throughout the endoscopic procedure. Taking an imaginary example if the total surgical time is 60 minutes then it may be hypothetically possible to operate the inflow pump independent of the pressure feedback mechanism for 55 minutes and under the control of the pressure feedback mechanism for 5 minutes. However, provision of operating the inflow pump 4 under a pressure feedback mechanism all through the endoscopic procedure can also be incorporated.

The Advantage of Operating the Inflow Pump Independent of the Pressure Feedback Mechanism:

The only reason for operating the inflow pump 3 independent of the pressure feedback mechanism is to avoid unnecessary corrections of minor pressure variations caused by physiological cavity wall contractions. The concept of physiological cavity wall contractions has been explained in detail under the heading 'basic physics of cavity distension'. In the present invention the physiological variations in cavity pressure are automatically corrected by the constriction site 8 without the need of a controller. If the cavity contracts a minute quantity of fluid which is pushed out of the cavity escapes via the constriction site 8 towards point 9. It is to be noted that the part of tube 7 between point 8 and 9 is at atmospheric pressure and the pressure created by a column of fluid in the fluid supply tube 2. Thus the fluid which is expelled from the cavity as a result of a physiological contraction escapes through the constriction site 8 against a pressure head which is equal to the pressure exerted by the vertical column of fluid in the fluid supply tube 2. However in context with FIG. 3 such pressure head is equal to atmospheric pressure. Thus, the transient, insignificant and instantaneous rise and fall in cavity pressure variations get stabilized at the desired preset value within a fraction of seconds. Alternatively if the cavity expands a suitable volume of fluid is sucked into the cavity from the irrigation circuit, such as from the region of point 10, and this is accompanied by a corresponding transient decrease in the flow rate at which fluid is escaping via the constriction site 8 in the direction of point 9 but if the magnitude of the said physiological expansion is more fluid may even be sucked into the cavity via the constriction site 8. This implies that the constriction site 8 is helping in maintaining a stable cavity pressure despite physiological cavity wall contractions by suitably varying the magnitude of an imaginary fluid flow vector passing through the constriction site 8. Normally the direction of such imaginary vector is always towards point 9 while its magnitude constantly varies to take care of the pressure changes resulting due to physiological cavity contractions. Normally a cavity continuously contracts and dilates by approximately the same magnitudes thus there is no logic to check the minor pressure variations emanating from the said contractions. Also the opening of the constriction site 8 does not allow the said physiological cavity pressure fluctuations to cause any significant cavity wall movement excursions by allowing to and fro movement of flow through its lumen. However, if the said pressure changes are made to be corrected by a controller, as is done in the prior art systems, the cavity wall may exhibit significant irregular pressure fluctuations which may result in significant movement excursions of the cavity wall, thus disallowing a predictably stable mechanical stabilization of the cavity walls. However, in the eventuality of fluid intravasation the fall in cavity pressure drop is relatively more permanent in nature thus needs to be corrected by the controller. As explained in the previous paragraph the controller is so programmed that the inflow pump 3 automatically comes under the pressure feedback control mechanism of the controller in case the cavity pressure alters by a desired minimum preset magnitude and for a desired preset time interval, thus a new 'RPM.final' is established at which the inflow pump is again allowed to operate without the feedback control of the controller. As a safety precaution a provision can be made in the controller via suitable input means to fix an upper safe limit 'RPM.final' and the cavity pressure P such that these safe limits are not exceeded accidentally.

Selection of a Suitable Diameter for the Constriction Site:

If the diameter of the constriction site 8 is very small then the said transient pressure fluctuation in the cavity pressure would be of a relatively larger magnitude and would last for a relatively longer time interval but the associated resultant movement excursion of the cavity wall would be of a relatively small amplitude. Similarly if the diameter of the constriction site 8 is very large then the said transient cavity pressure fluctuations would be of a relatively smaller magnitude and would last for a relatively shorter time interval but the associated resultant movement excursion of the cavity walls would be of a much larger amplitude. These statements are explained by the help of three hypothetical numerical assumptions as stated in table 1 which is as follows:

TABLE 1

| Serial number of the assumption | A hypothetically assumed numerical value of the construction site diameter | A hypothetically assumed numerical value of the magnitude of a transient pressure surge associated with a physiological cavity wall contraction movement | A hypothetically assumed time interval for which the said pressure surge exists | A hypothetically assumed magnitude of the associated resultant cavity wall movement excursion |
|---|---|---|---|---|
| 1 | 0.1 mm | 20 mm Hg | 3 seconds | 0.5 mm |
| 2 | 1 mm | 5 mm Hg | 1 second | 1 mm |
| 3 | 1.5 mm | 1 mm Hg | 0.5 seconds | 5 mm Hg |

(*Note:
A similar table can be hypothetically constructed taking into consideration cavity wall expansion, instead of contraction.)

In context with routine endoscopic procedures the above mentioned hypothetical situation associated with serial number 2 is most acceptable out of the three hypothetical examples because a high magnitude cavity wall movement excursion is not at all desirable while a moderately high transient pressure surge may be acceptable in most endoscopic procedures. Thus the nuisance value of a cavity wall movement excursion is relatively more than the nuisance value of the said transient pressure surge. However the amplitude of the pressure surge should also be not very high because it may promote intravasation and other problems.

Thus while selecting the diameter of the constriction site two things are kept in mind, the operational needs of the endoscopic procedure as already explained in this paragraph and the anticipated cavity wall contraction and expansion movements. Thus in those endoscopic procedures where mechanical stability of the cavity walls is important the numerical value of the constriction site diameter D should be relatively smaller.

Limiting and Predicting Cavity Pressure Surge in Case of Accidental Outflow Obstruction:

If an abnormally high pressure develops inside a tissue cavity during endoscopic surgery it may cause mechanical rupture of the cavity and may also lead to dangerous intravasation. Referring to FIG. 4 if during endoscopic surgery the outflow tube is accidentally blocked the cavity pressure does not increase to dangerous levels because the controller automatically instructs the pump 3 to work at a reduced inflow flow rate, thus a surgical complication is avoided. Referring to the system shown in FIG. 2 if the outflow tube 12 is accidentally blocked the cavity pressure may rise to a dangerously high value in the absence of a controller. In context with FIG. 2 an accidental obstruction of the outflow tube or a deliberate obstruction of the inflow tube as achieved by willfully closing the inflow port, both the situations result in a steeply rising pressure as measured by the transducer 5. Thus, while using the mechanical version of the invention as shown in FIG. 2, it is suggested that before starting the endoscopic surgery the surgeon should deliberately block the distal end of the inflow tube 4 by closing the inflow port of the endoscope and note the resultant maximum pressure rise. If the resultant pressure is higher than the maximum prescribed safe cavity pressure, then the diameter of the constriction site can be increased by some magnitude such that the resultant pressure created by blocking the inflow tube is well below the maximum safe pressure prescribed for the tissue cavity. In this manner, for a mechanical system as shown in FIG. 2, for a specific inflow rate, the maximum resultant pressure that would develop inside the cavity in the case of a block in the outflow tube can be predictably known and limited. Such method of knowing and limiting the rise in cavity pressure as a result of outflow tube obstruction does not have much role in the controller based version of the invention as shown in FIG. 4. However, even if the controller based version of the invention as shown in FIG. 4 is being used and a high out flow rate is being used then if the outflow tube is suddenly obstructed a transient pressure surge of a relatively small or large amplitude may be experienced before the controller finally stabilizes the inflow pump rotation speed at a significantly reduced value to maintain the initially desired preset cavity pressure. Such pressure surge occurs because initially the pressure transducer senses an exponentially increasing cavity pressure, next a corresponding feedback signal is sent to the controller and the controller finally acts by reducing the rotational speed of the inflow pump and all these actions may take a few seconds to be implemented, especially if the inflow pump was operating at a very high speed of rotation, and in this short time interval a transient surge in the cavity pressure may be experienced. The amplitude of such pressure surge would be small due to the controller feedback mechanism but even a small magnitude surge may damage fragile tissues, for example tissue inside a brain tissue cavity. The amplitude of the said surge can be predictably reduced by suitably increasing the value D. Thus a relatively higher value of D enhances patient safety by predictably limiting the maximum pressure which can develop inside the cavity in case of an accidental obstruction of the outflow tube 12 if the mechanical version of the invention is being used and it also predictably limits the amplitude of any small amplitude pressure surge which might occur when the inflow tube is accidentally blocked while the controller based version of the invention is being used. It has been described in the previous paragraph that the operational efficiency of the system also improves if the value of D is increased. Thus a suitable value of D can be selected by keeping into consideration patient safety and system efficiency. Once a suitable value for D is selected it never altered thereafter as has already been discussed previously. The system shown in FIGS. 1 to 4 can also have the provision of incorporating multiple constriction sites having different diameters. D to suit and accommodate the operational needs of multiple type of endoscopic procedures.

A Variable Constriction Site

In context with the system shown in FIG. 4 it is also possible to have a system in which the cavity pressure is maintained and regulated by continuously varying, by the help of a controller, the diameter D at the constriction site 8. The diameter D at the constriction site 8 could also be intermittently regulated by a controller as and when required for example in the eventuality of fluid intravasation or extravasation thus implying that the diameter D shall be free from the influence of the controller for most of the time and shall be brought under the influence of the controller only when needed and that also for only a small part of the total surgical time. Such a concept has been described in great detail in the previous paragraphs in context with FIG. 4. In the variable constriction system proposed in this paragraph both pumps 3 and 14 would always operate at constant RPM's and the cavity pressure would be regulated only by varying the diameter D at the constriction site 8. At the start of the surgery the 'RPM.inflow' and outflow rate R2 would need to be set by feeding suitable values into the controller after which the controller would not influence or regulate the RPM's of the two pumps and the cavity pressure would be maintained only by varying the diameter D at the constriction site 8. In order to vary the diameter at the constriction site 8 a suitable electromechanical devise such as a solenoid operated devise could be installed over the housing tube 7 and the controller could increase or decrease the value D. Such a devise is not a devise which would either totally close or totally open the lumen of the pipe. By the help of the said devise the lumen diameter would be varied in a controlled manner and not just by totally opening or totally closing the lumen. The said devise could comprise of a long coil containing a movable long cylindrical magnet and this magnet piece by pressing over the tube, would vary the inner diameter of the tube. When current passes through such coil the magnet piece would either be pulled in or pushed out depending upon the direction of the current and the polarity of the magnet and the force which the said long cylindrical magnet piece could apply over the plastic tube would depend upon the current density passing through the coil or in simpler terms the amount of electrical energy supplied to the coil. In context with the present paragraph the controller shall regulated the amount of electrical energy supplied to the coil such that the magnetic rod presses over the tube with an adequate force and the inner diameter of the pipe would depend upon such force. Thus the inner diameter of the tube shall be a function of the current density. However, the said electromagnetic devise described in this paragraph has not been included in any of the diagrams only to keep the drawings simple.

The Main Invention

FIGS. 2 to 4 have been discussed only to help in understanding the system of the main invention which is shown in FIG. 1. One basic difference between FIG. 1 and FIGS. 2 to 5 is that in FIG. 1 'a pressure pulse dampening system' has been included inorder to dampen the pressure pulsations in the tissue cavity caused by the outflow positive displacement pump, that is the peristaltic pump 14. The said 'pressure pulse dampening system' shall be described in detail in the next paragraph.

A Method to Dampen the Pressure Pulsations Caused by the Outflow Positive Displacement Pump Referring to FIG. 2 the outflow positive displacement pump, that is the outflow peristaltic pump 14 creates pressure pulsations which are invariably transmitted to tissue cavity leading an undesirable turbulence inside the tissue cavity. Referring to FIG. 1 the fluid pressure, such as at a point 39, is pulsatile in nature because the peristaltic pump 5 constantly extracts fluid from the tissue cavity via the outflow tube 12 in a pulsed manner and not in a continuous manner and this leads to fluid pressure pulsations. The said pulsations are transmitted to the tissue cavity 11 in a retrograde manner via the outflow tube 12. Hypothetically assuming that the pump 14 rotates at fixed RPM then in that case the frequency of such pulsations would remain uniformly the same all through the operation of the pump. If a graph is plotted for the said pulsations, by relating the fluid pressure to the 'Y' axis and the time to the 'X' axis, then such graph would have a uniform shape having positive and negative pressure swings of a predictably fixed amplitude and fixed frequency. It is to be noted that as the pump RPM is increased the frequency as well as the amplitude of the said pressure swings also increase. The said pulsations are produced because each time any one roller of the peristaltic pump comes in apposition with a fixed point, for example the inlet end of the peristaltic pump 14, some fluid is withdrawn from the outflow tube 12 by the outflow peristaltic pump via its inlet end in the form of a bolus. The wave form of such pulsations need not be sinusoidal, but for the sake of an easier understanding let the said waveform be hypothetically assumed to be sinusoidal in nature. As already stated, if the pump RPM increases then along with the frequency the amplitude of the said waveform also increases. When the pump 14 rotates in the direction of the curved arrow fluid is extracted from the outflow tube 12, the cavity 11 and the inflow tube 4 and let all three of these collectively be termed as 'fluid extraction region'. In physical terms the said pressure pulsations are produced because the fluid tends to be extracted from the 'fluid extraction region' in the form of regular pulses wherein each pulse corresponds to a fixed volume of fluid pulled by a roller from the 'fluid extraction region' in the form of a bolus of fluid. Thus the motion of each roller would correspond to one complete sinusoidal pressure wave. Thus the motion of each roller would correspond to one complete sinusoidal pressure wave, assuming that the said waveform has been assumed to be sinusoidal as previously stated. The movement of a single roller in relation to a fixed point such as the inlet end of the pump can be hypothetically divided into three parts, that is, part one when the roller approaches the said point, part 2 when the roller is in apposition with the said point and part 3 when the roller moves away from the said point. Let the parts 1, 2 and 3 be collectively termed as 'single roller movement' and the time taken to accomplish the said 'single roller movement' be termed as 'single roller time'. Assuming the pressure waveform to be a sinusoidal curve, each 'single roller movement' corresponds to one complete sinusoidal pressure waveform consisting of a positive pressure pulse followed by a negative pressure pulse or vice versa. Also the time period of the assumed sinusoidal wave form would be equal to 'single roller time'. If during a negative pressure pulse an adequate volume of fluid is removed from the 'fluid extraction region' and during a positive pressure pulse the same adequate volume of fluid is again added back into the 'fluid extraction region' the sinusoidal nature of the pressure waveform could get dampened and the resultant waveform would get transformed into an almost straight line curve. The resultant waveform could theoretically be an absolute straight line if the wave form associated with the said process of adding and removing adequate volumes of fluid from the 'fluid extraction region' absolutely resembled with the wave produced as a result of the pulsatile flow of the peristaltic pump and the phase difference between the two waves was exactly 180 degrees however this may not be achieved in practical situations. However a substantial dampening of the resultant waveform could be practically achieved if a syringe system was synchronously coupled with the outflow peristaltic pump 14 and the single outlet end of the said syringe system was connected with the 'fluid extraction region'.

Figure 6:
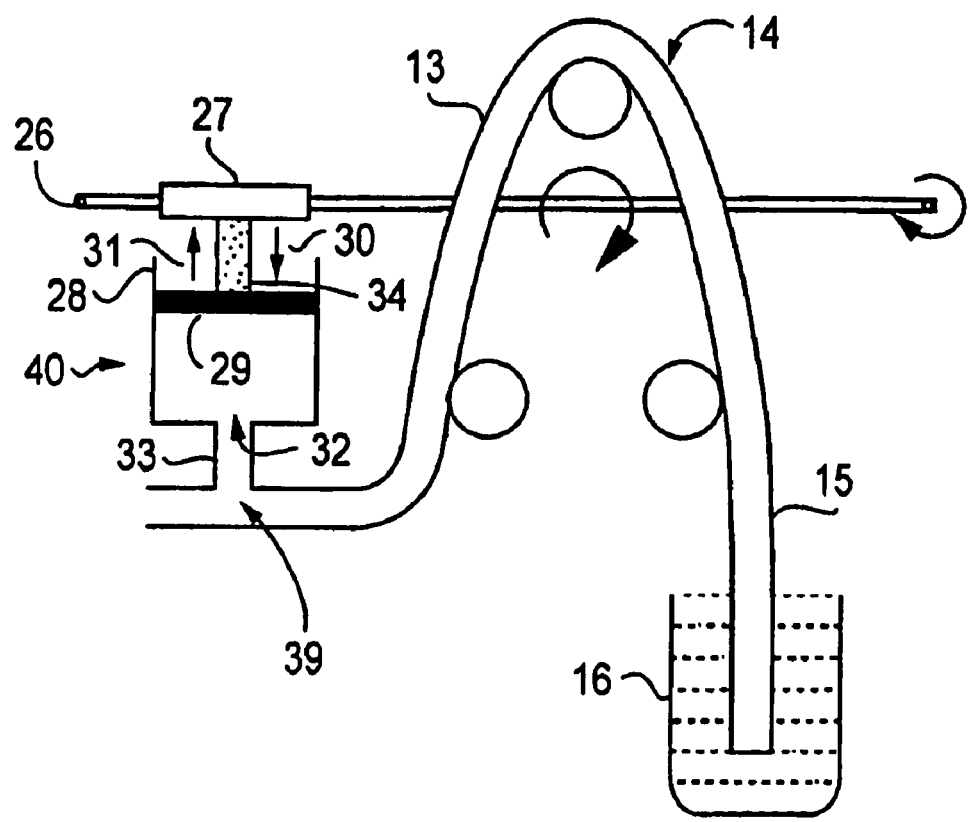
FIG. 6 shows the syringe system.

The said syringe system is shown in FIG. 6. The syringe system 40 consists of a piston 29 denoted by a shaded area and the piston 29 moves up and down inside a cylinder 28 while making a watertight contact with the inner walls of this cylinder 28. One end of a straight rod 34 is connected to the piston while the other end of this rod 34 is connected to a coupling mechanism 27 housed on a common rotating shaft 26. The coupling mechanism 27 and the peristaltic pump 14, both are attached on this common shaft 26. The coupling mechanism 27 is so designed that it converts the rotary motion of the shaft 26 into a linear up down motion of rod 34 which is ultimately manifested as an up down movement of piston 29 inside the cylinder 28. The up down motion of the rod 34 is denoted by arrows 31 and 30. Thus the shaft 34 is a common shaft which mechanically operates both, pump 14 as well as the syringe system 40. The direction of rotation of the shaft 26 is denoted by a curved arrow located at the right end of the shaft 26. The syringe system 40, as the name suggests, resembles a hypodermic syringe used for giving injections to patients. Obviously, the syringe system 40 has only one single opening 32. A tube 33 extending between the opening 32 and the outflow tube 12 connects the syringe system to the outflow tube 12. Tube 12 is a part of the said 'fluid extraction region' described in the previous paragraph. Thus the syringe system can be considered to be connected with the said 'fluid extraction region'. The opening 32 can be referred to as an 'outlet end' or an 'inlet end' because the syringe system can push as well as pull fluid from the 'fluid extraction region'. However for the sake of convenience henceforth the opening 32 shall be termed as the outlet end of the syringe system 40. The coupling mechanism 27 is so designed that the vertical movements of the syringe system can be accurately synchronized with the rotary motion of the peristaltic pump 14. The piston 29 can move up>down>up or down>up>down, depending upon the initial position of the piston at the start of the motion and let each such movement of the piston be termed as a 'complete piston movement'. The coupling mechanism 27 is so designed that while the peristaltic pump 14 rotates by 360 degrees the syringe system correspondingly exhibits 'complete piston movements' which are equal to the number of the rollers of the peristaltic pump. Thus for a peristaltic pump which has three rollers then for each 360 degrees rotation of the peristaltic pump the syringe system exhibits three 'complete piston movements' while for a peristaltic pump with four rollers four 'complete piston movements' would occur for each 360 degree rotation of the peristaltic pump. The syringe system is synchronized with the peristaltic pump via the coupling mechanism 27 in such manner that while a roller of the peristaltic pump produces a negative pressure pulse the syringe system pushes fluid into the 'fluid accumulation region' and while the same roller produces a positive pressure pulse the syringe system pulls out an equivalent volume of fluid from the 'fluid accumulation region'. In order to dampen the pulsations of the peristaltic pump, besides mechanically synchronizing the syringe system with the peristaltic pump, the volume of fluid pulled in or pushed out of the syringe system corresponding to each upward or downward movement of the piston also has to be accurately adjusted, and the same may be done manually by a 'hit and try method'. The volume of fluid pulled in or pushed out by the syringe system depends upon the linear movement excursion of the piston 29. Also the magnitude of the downward piston excursion is equal to the magnitude of the upward piston excursion, thus the volume of fluid pushed out is always equal to the volume of fluid pulled in during each downward or upward movement. Thus the coupling mechanism 27 has two functions, synchronization of the syringe system with the peristaltic pump and adjusting the volume of fluid pulled in or pushed out by the syringe system for each upward or downward movement of the piston. The synchronization and the determination of the said volume to be pushed out or pulled into the syringe system are done manually such that a substantial dampening of the pressure pulsations is achieved and once this is achieved the synchronization at the level of the coupling 27 is never again disturbed and the volume of fluid pulled in or pushed out of the syringe system for each movement excursion is also not changed thereafter. After the coupling 27 is adjusted with respect to synchronization and the volume of fluid to be pulled in and pushed out, the peristaltic pump pulsations shall continue to remain dampened independent of the peristaltic pump RPM and the nature of rotation, that is fixed or variable RPM. In simpler terms the peristaltic pump pulsations would continue to remain dampened even at a high pump RPM. Also the point at which the syringe system 40 is connected to the said 'fluid extraction region', for example the outflow tube 12, then the position of such a point should also not be changed thereafter because this may bring about a phase difference between the waveform related to the peristaltic pump pulsations and the waveform related to the syringe system pulsations, thus the resultant dampening could no longer be satisfactory. Also preferably the outlet tube 33 of the syringe system should be connected as close to the outlet end of the inflow peristaltic pump as possible.

Figure 7:
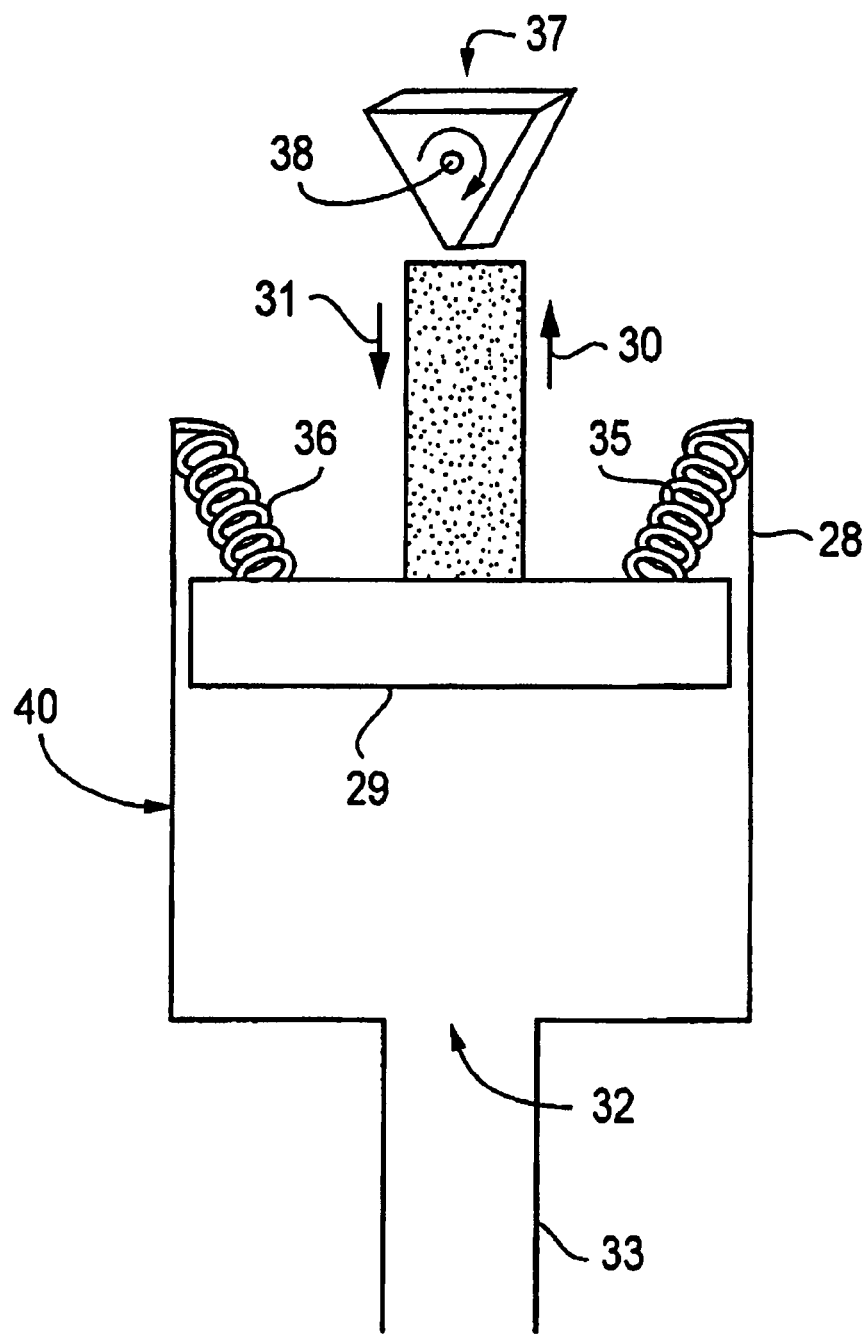
FIG. 7 shows a spring based design for the syringe system.

The coupling 27 can be compared to some extent with the conventional CAM system present in automobile engines. Any specific mechanical design for the coupling 27 is not important, it is the resultant function of the coupling 27 with respect to the piston movement, as already described, which is important. The coupling 27 can have many mechanical designs. FIG. 7 shows one such possible mechanical design for the coupling 27. In FIG. 7 a small length of the common shaft 26, which is related to the coupling 27, has been made of triangular shape as seen in its cross sectional view and the same is labeled as 37. Let this triangular part 37 be termed as the 'piston coupler'. The edges of the piston coupler are shown sharp however they could preferably be rounded to suit various operational needs. Similarly the size of the 'piston coupler' could also be increased or decreased in order to decrease or increase the volume of fluid displaced by the cylinder during a downward or upward movement of the piston. The central axis point of the 'piston coupler' is denoted by point 38. In case the dimensions of the 'piston coupler' are chosen to be relatively larger than the dimension of the common shaft 26, the point 38 could also represent the point at which the common shaft 26 passes through the 'piston coupler' and in such a situation the 'piston coupler' 37 could be manually rotated on the common shaft 26 in a clockwise or anti clockwise direction and then locked mechanically at a position which provides the most accurate synchronization. The springs 35 and 36 extending between the inner walls of the cylinder and the piston exert a constant and substantially large upward pull on the piston 29 which causes the rod 34 to constantly be in apposition with the 'piston coupler' 37. The springs can be one or more than one in number and the springs can also be substituted by any other mechanical means also which provide an active upward movement of the piston. The 'piston coupler' 37 is assumed to be able to apply a substantially large downward force on the piston 29 via rod 34 such that a corresponding transient negative fluid pressure inside the cylinder can be totally neglected in the face of the said large substantial downward force. Similarly the springs 35 and 36 are capable of pulling up the piston with a substantially large force such that a corresponding transient positive fluid pressure pulse inside the cylinder could be totally neglected. The idea is that the downward movement of the piston should not be aided by the negative pressure pulse inside the cylinder, this downward movement should be an active movement for which energy is to be derived from the springs from the shaft 26. Similarly the upward movement of the piston should not be aided by the positive pressure pulse inside the cylinder, this upward movement should be an active movement for which energy is to be derived from the springs 35 and 36. The energy for the said upward movement of the piston could also be derived from the shaft 26 if suitable mechanical provision facilitating an active upward movement of the piston could be provided at the level of the coupling 37.

It is important to note that it is not mandatory to use the said 'pressure pulse dampening system' with a peristaltic pump only as, with suitable mechanical modifications, the 'pressure pulse dampening system' could be used beneficially with any type of a positive displacement pump.

The 'pressure pulse dampening system' could also be a mechanism like the 'piston coupler' shown in FIG. 7 whose rounded edges could directly impinge on a suitable area situated on the outer surface of the 'fluid extraction region' in a uniform synchronized manner, as described, such that this results in continuous uniform synchronized variations in the total volume capacity of 'fluid extraction region'. The said suitable area on the outer surface of the 'fluid extraction region' could be a membrane made consisting of a strong resilient polymeric material having an adequate elasticity. The said membrane should also be sufficiently thick and should have an adequate elasticity such that an outward movement of such membrane, a movement related to the upward pull by the said springs, applied a substantially larger force in comparison to force related with the transient corresponding pressure pulse.

A System of Incorporating Multiple Peristaltic Pump Tubes

In the preceding parts of the manuscript the peristaltic pump 14 is shown to have one single tube 13 which come in contact with the rollers of the peristaltic pumps. Arbitrarily referring to the outflow pump 14, $$R2 = \frac{\pi \times B^2 \times L}{4} \times RPM$$

where R2=Flow rate of pump 14, B=inner diameter of the peristaltic pump tube 4, L=length of tube 4 and RPM=revolution per minute of pump 5. If the value B is doubled then for the same RPM the flow rate R2 doubles. Similarly if L doubles then also for RPM the flow rate R2 doubles. However keeping in mind the mechanical constraints the values B and L cannot exceed a certain practical value. However if two tubes like tube 4 are used in parallel in the pump 14 then the mathematical expression for the flow rate could be written as follows:

$$R2 = \frac{\pi \times B^2 \times L}{4} \times RPM \times 2$$

This implies that if two peristaltic pump tubes are used instead of one single tube then the flow rate becomes double for the same RPM and if three tubes are used then the flow rate becomes three times and so on. The frequency of the 'pressure pulsations' created by a peristaltic pump is directly proportional to the pump RPM. The said 'pressure pulsations' are undesirable thus it is helpful to keep their frequency as minimal as possible if the flow rate is not compromised. Thus this system of incorporating two or more peristaltic pump tubes helps in attaining a higher flow rate for a relatively lesser RPM. It is but obvious that the said two or more than two parallel tubes are connected to each other at the inlet and the outlet ends of the peristaltic pump.

Determination of the Instantaneous Real Time Rate of Fluid Intravasation

Fluid intravasation is a process by which the irrigation fluid enters into the patient's body system and if excess volume of fluid is intravasated it can be dangerous to the patient's life. Thus, keeping in mind surgical safety, it is extremely important to constantly know the rate at which such intravasation occurs so that corrective surgical measures can be taken before a dangerous volume of fluid intravasates. The inventors propose that one fluid flow rate sensor each be incorporated in the inflow tube and the outflow tube. Referring to FIG. 1 inflow flow rate sensor 88 is located in the inflow tube 4 anywhere between the inlet port of the endoscope and the point at which the distal end of the constriction site housing tube 7 is connected to the inflow tube 4 as at point 10. Such a flow rate sensor 88 measures the rate at which fluid enters into the tissue cavity 11 and the same is being termed as 'cavity inflow rate'. Obviously the 'cavity inflow rate' is the true inflow rate for the tissue cavity. Similarly outflow flow rate sensor 99 is located anywhere in the out flow tube between the outflow port of the endoscope and the inlet end of the outflow peristaltic pump 14 or any other outflow positive displacement pump. However if an additional or optional constriction site housing tube 24 is also connected to the out flow tube 12 as shown in FIG. 4 then the outflow flow rate sensor should be located between the outflow port of the endoscope and the point at which the proximal end of the constriction site housing tube 24 is connected to the outflow tube 12. The outflow flow rate sensor measures the rate at which fluid is extracted from the tissue cavity which is the same as R2 that is the flow rate of the outflow pump. Now the real time rate of fluid intravasation, being termed as R3, can be determining by subtracting R2 from the 'cavity inflow rate', the mathematical expression for the same being can be written as R3=Cavity inflow rate-R2. The said flow rate sensors 88, 99 should be accurate, reliable, easy to install and should not have any movable parts. The inventors suggest that the said sensors 88, 99 comprise of a heating coil in physical contact with a metal plate for heating the same and a temperature sensor placed in contact with the metal plate, the temperature of the metal plate being a function of the fluid flow rate. The said flow rate sensors 88, 99 are electrically connected with a micro-controller which automatically subtracts R2 from the 'cavity inflow rate' to give the value R3. The value R3 can also be further integrated with respect to time to give the total volume of fluid intravasated over a certain time interval. The said temperature related flow rate sensors 88 99 could be a 'hot wire anemometer'.

Determination of the Real Time Rate of Fluid Intravasation without Using Fluid Flow Rate Sensors The tissue cavity pressure P is a function of the RPM of the inflow centrifugal pump 3, that is 'RPM.inflow', the cavity outflow rate (R2) and the real time rate of intravasation (R3). The pressure at the outlet end of the centrifugal pump is a hyperbolic function of the centrifugal flow rate. The value P increases as the value 'RPM.inflow' increases and decreases as R3 and R2 increase. Thus a mathematical expression could be derived which contains P, 'RPM.inflow', R2 and R3. Such a mathematical expression could be fed into a controller and in this manner the value R3, the real time rate of fluid intravasation could be determined.

The proposed invention can also be used to impart endoscopic training skills by the help of endoscopic experimental models based on the present invention. Also use and scope of the present invention is not limited to human tissue cavities and it may be used for performing multiple endoscopic procedures in animal tissue cavities also and also for imparting training in endoscopic surgeries related to animal tissue cavities.

It is believed that the foregoing description conveys the best understanding of the objects and the advantages of the present invention. It will be understood by those skilled in the art that numerous improvements and modifications may be made to the embodiments of the invention disclosed herein without departing from the departing from the spirit and scope thereof.

The Heart and Soul of the Invention

The constriction site 8 as described in the manuscript is the heart and soul of the invention without which the invention cannot exist.

Advantages of the Proposed Invention

The proposed invention makes endoscopic procedures extremely safe, simple, more accurate and easy to perform. The proposed invention helps the surgeons to perform endoscopic surgeries with greater safety and confidence especially in the initial phase of their learning curve. Also a distending system based on the proposed invention can be used in multiple endoscopic procedures thus reducing the financial burden on the hospital and the patient. The advantages of proposed invention are summarized in the following table along with the corresponding disadvantages of the prior art systems:

| ADVANTAGES OF THE PRESENT INVENTION: | DISADVANTAGES OF THE PRIOR ART SYSTEMS: |
| --- | --- |
| It is possible to create and maintain a desired precise tissue cavity pressure for a desired precise fixed outflow rate including a zero outflow rate. | This is not possible in any prior art system. |
| It is possible to reduce the amplitude of the pressure pulsations created by an outflow positive displacement pump to an almost negligible magnitude irrespective of the pump RPM. | This is not possible in any prior art system. |
| It is possible to reduce the frequency of the pressure pulsations created by an outflow positive displacement pump for the same outflow rate. | Such system is not present in any prior art system. |
| A predictably constant desired fluid pressure can be maintained inside a tissue cavity for indefinite time. | This is not possible in any prior art system. |
| A predictably constant desired fluid pressure can be maintained inside a tissue cavity for indefinite time despite physiological cavity wall contractions. | This is not possible in any prior art system. |
| A predictably constant clear endoscopic visualization is possible. | This is not possible in any prior art system. |
| It is possible to achieve a predictably stable mechanical distension of the cavity walls. | This is not possible in any prior art system. |
| It is possible to minimize cavity fluid turbulence to almost negligible levels. | This is not possible in any prior art system. |
| The instantaneous real time rate of fluid intravasation into the patient's body is constantly known by using a hot wire anemometer type of a flow rate sensor. | Such feature is not present in any prior art system. |

CONCLUSION

The proposed invention is novel and unique. The invention relates not only to increasing surgical efficiency in certain endoscopic procedures but it also helps in preventing human morbidity and human mortality in many endoscopic procedures. Thus the proposed invention is extremely useful for entire mankind.

We claim:

1. A system for distending body tissue cavities of subjects by continuous flow irrigation during endoscopic procedures the system comprising:

a fluid source reservoir containing a non viscous physiologic fluid for continuous flow irrigation during an endoscopic procedure;

a fluid delivery tube connecting the fluid source reservoir to an inlet end of an inflow dynamic pump an outlet end of the pump being connectable to a tissue cavity subjected to the endoscopic procedure through an inflow tube for pumping the fluid at a controlled flow rate into the cavity to obtain a distended cavity, the rate at which the fluid from the inflow tube enters into the tissue cavity being termed as the cavity inflow rate;

a positive displacement outflow pump having an inlet end being connectable to the tissue cavity through an outflow tube for removing the fluid from the cavity at a controlled flow rate, the flow rate of the outflow pump being termed as the cavity outflow rate;

an outlet end of the outflow pump connected to a waste fluid collecting container via a waste fluid carrying tube; and a tube having a fixed constriction site provided between the fluid source reservoir and the inflow tube such that the same by-passes the inflow pump, the constriction site having a fixed diameter, wherein the tube provides a route for any excess fluid being pumped by the inflow pump to bypass the inflow pump and return to the fluid supply tube or the fluid source reservoir;

an outflow pressure pulsation dampening means provided between the cavity and the positive displacement outflow pump, and connected to the outflow tube for dampening the pressure pulsations inside the cavity caused by the positive displacement outflow pump, wherein the pressure dampening means comprises a single outlet syringe mechanism, a piston of the same being coupled synchronously to the positive displacement outflow pump through coupling means and the single outlet end of the syringe mechanism being connected to the outflow tube.

* * * * *